US007160684B2

(12) United States Patent
Argentieri et al.

(10) Patent No.: US 7,160,684 B2
(45) Date of Patent: Jan. 9, 2007

(54) METHODS OF SELECTING COMPOUNDS FOR MODULATION OF BLADDER FUNCTION

(75) Inventors: Thomas M. Argentieri, Yardley, PA (US); Jeffrey H. Sheldon, Trappe, PA (US)

(73) Assignee: Wyeth, Madison, NJ (US)

( * ) Notice: Subject to any disclaimer, the term of this patent is extended or adjusted under 35 U.S.C. 154(b) by 40 days.

(21) Appl. No.: 10/399,489

(22) PCT Filed: Oct. 17, 2001

(86) PCT No.: PCT/US01/32371

§ 371 (c)(1),
(2), (4) Date: Apr. 17, 2003

(87) PCT Pub. No.: WO02/32960

PCT Pub. Date: Apr. 25, 2002

(65) Prior Publication Data

US 2005/0101004 A1 May 12, 2005

Related U.S. Application Data

(60) Provisional application No. 60/241,078, filed on Oct. 17, 2000, provisional application No. 60/281,428, filed on Apr. 4, 2001.

(51) Int. Cl.
C12Q 1/68 (2006.01)
G01N 33/567 (2006.01)
C12N 5/06 (2006.01)
C12N 5/10 (2006.01)
C12N 5/08 (2006.01)

(52) U.S. Cl. .......................... 435/6; 435/365; 435/366; 435/7.21

(58) Field of Classification Search .................. 435/6
See application file for complete search history.

(56) References Cited

U.S. PATENT DOCUMENTS

| | | | | |
|---|---|---|---|---|
| 6,133,275 A | * | 10/2000 | Ehrlich et al. | 514/267 |
| 6,277,978 B1 | * | 8/2001 | Keating et al. | 536/23.5 |
| 6,348,486 B1 | * | 2/2002 | Argentieri et al. | 514/411 |
| 6,403,360 B1 | * | 6/2002 | Blanar et al. | 435/243 |
| 6,413,719 B1 | * | 7/2002 | Singh et al. | 435/6 |
| 6,455,568 B1 | * | 9/2002 | Jenkins et al. | 514/415 |
| 6,582,913 B1 | * | 6/2003 | Keating et al. | 435/6 |
| 6,613,786 B1 | * | 9/2003 | Hewawasam et al. | 514/384 |
| 6,617,131 B1 | * | 9/2003 | Steinmeyer et al. | 435/69.1 |
| 6,635,660 B1 | * | 10/2003 | Jenkins et al. | 514/323 |
| 6,767,736 B1 | * | 7/2004 | Hu et al. | 435/320.1 |
| 6,794,161 B1 | * | 9/2004 | Jentsch | 435/69.1 |
| 2002/0137746 A1 | * | 9/2002 | Carl et al. | 514/241 |
| 2004/0197825 A1 | * | 10/2004 | Karicheti et al. | 435/7.1 |
| 2005/0037460 A1 | | 2/2005 | Jentsch | |
| 2005/0059823 A1 | * | 3/2005 | McNaughton-Smith et al. | 544/13 |
| 2005/0101004 A1 | * | 5/2005 | Argentieri et al. | 435/252.3 |

FOREIGN PATENT DOCUMENTS

| | | | |
|---|---|---|---|
| DK | WO 00/44786 | * | 8/2000 |
| EP | 1326597 | * | 12/2005 |
| WO | WO 99/07832 A1 | | 2/1999 |
| WO | WO 99/21875 A1 | | 5/1999 |
| WO | WO 00/44786 A1 | | 8/2000 |
| WO | WO 01/01970 A2 | | 1/2001 |
| WO | WO 02/32419 A2 | | 4/2002 |

OTHER PUBLICATIONS

MedLine Plus Medical Encyclopedia, A.D.A.M., Inc. online last update May 3, 2002.*
Kubisch et al, Cell, 1999, 96/3:437-446.*
Hewawasam et al, Bioorganic and Medicinal Chemistry Letters, 2002, 12:1117-1120.*
Dmochowski et al, Urology, 2000, 56/Suppl. 6A:41-49.*
Andersson, Best Practice and Research Clinical Obsterics and Gynaecology, 2000, 14/2:291-313 Abstract Only.*
Wang et al, Science, 1998, 282:1890-1893.*
Smith et al, J. Neuroscience, 2001, 21/4:1096-1103.*
Butera et al, Bioorganic and Medicinal Chemistry Letters, 2001, 11:2093-2097.*
Woods et al, J. Urology, 2001, 166/3:1142-1147 Abstract Only.*
Gilbert et al, J. Medicinal Chemistry, 2000, 43/6:1203-1214 Abstract Only.*
Butera et al, J. Medicinal Chemistry, 2000, 43/6:1187-1202 Abstract Only.*
Wein et al, Urology, 1998, 51/2A Suppl.:43-47 Abstract Only.*
Levin et al, Pharmacology, 1992, 45/1:1-8 Abstract Only.*
Butera et al, Drugs of the Future, 2000, 25/3:239-245 Abstract Only.*
Wojdan et al, J. Pharmacology and Experimental Therapeutics, 1999, 289/3:1410-1418 Abstract Only.*
Antane et al, Book of Abstracts, 218th ACS National Meeting, New Orleans, Aug. 22-26, 1999.*
Sudoh et al, J. Autonomic Pharmacology, 1997, 17/2:91-96 Abstract Only.*
Gutman et al, Pharmacological Reviews, 2003, 65/4:583-586.*

(Continued)

*Primary Examiner*—N. M. Minnifield
(74) *Attorney, Agent, or Firm*—Darby & Darby

(57) ABSTRACT

The present invention involves an assay system and method of selecting compounds useful in the treatment of bladder instability and related bladder conditions through the activation of KCNQ potassium channels in the bladder smooth muscle.

57 Claims, 4 Drawing Sheets

OTHER PUBLICATIONS

Andersson, Urology, 2000, 55/Suppl 5A:51-57.*
Thorneloe et al, J. Physiol., 2003, 549.1:65-74.*
Wein, Exp. Opin. Invest. Drugs, 2001, 10/1:65-83.*
Michel, Urologe A., Jun. 2003, 42/6:807-811 abstract only.*
Butera et al, Bioorganic and Medicinal Chemistry Letters, 2005, 15:2495-2501.*
Meredith et al, JBC, Aug. 27, 2004, 279/35:36746-36752.*
Wickenden et al, Characterization of the KCNQ5/Q3 potassium channels expressed in mammalian cells. Dr. J. Pharmacol., 2001, 132:381-384.*
Main et al, Molecular Pharmacology, 2000, 58:253-262.*
Rundfeldt et al, Neuroscience Letters, 2000, 282:73-76.*
Hashitani et al, J. Physiology, 2000, 524.2:565-579.*
Rogawski, Trends in Neuroscience, 2000, 23:393-398.*
Herrera et al, Am. J. Physiol. Cell Physiol., 2001, 280:C481-C490.*
Shapiro et al, J. Neuroscience, Mar. 1, 2000, 20/5:1710-1721.*
Wickenden et al, Molecular Pharmacology, 2000, 58/3:591-600.*
Susumu et al., Japanese J. Pharm. (2000) 82:Suppl. 1:135P, 73rd Annual Meeting of the Japanese Pharmacological Society, Yokohama, Japan, Mar. 23-25, 2000. Abstract.
Sugimoto et al., J. Membrane Biol. (1990) 113:1:39-48 and BIOSYS Online! Biosciences Information Service, Phila. PA (1990) Database accession No. PREV199089080542. Abstract.
Huber et al., Am. J. Physiol. (2000) 279:1(part 2):F65-F76.
Vallon et al., J. Am. Soc. Nephrol. (2001) 12:10:2003-2011.
Tomoyuki et al. Japanese J. Physiol. (2002) 52:1:31-39 and BIOSYS Online!Biosciences Information Service, Phila. PA (2002) Database accession No. PREV200200284496. Abstract.
Sheldon, J. H. et al., (2002) ASPET-Ray Fuller Symposium, Lower Urinary Tract Disorders: Physiology, Pharmacology & Therapeutic Approaches, San Francisco, CA, Jul. 2002.

* cited by examiner a.

b.

a.

10 min.  ↑ Retigabine (10 mg/kg, i.p.)

b.

METHODS OF SELECTING COMPOUNDS FOR MODULATION OF BLADDER FUNCTION

CROSS REFERENCE TO PRIOR APPLICATION

This is a U.S. National Phase application under 35 U.S.C. §371 of International Patent Application No. PCT/US01/32371, filed Oct. 17, 2001, which claims priority to U.S. Provisional Patent Application Ser. No. 60/241,078, filed on Oct. 17, 2000 and U.S. Provisional Patent Application Ser. No. 60/281,428, filed on Apr. 4, 2001. The International Application was published on Apr. 25, 2002 as WO 02/32960 A2 under PCT Article 21(2).

FIELD OF THE INVENTION

The present invention relates to the fields of pharmaceutical chemistry and urology and to a method of selecting compounds useful in the treatment of urologic conditions and to methods of treatment of said urologic conditions and, more particularly, to an assay system and method of selecting compounds useful in the treatment of bladder instability and related bladder conditions through the activation of KCNQ potassium channels in the bladder smooth muscle.

The invention also relates to a method of treatment for bladder instability by activating KCNQ potassium channels in the bladder smooth muscle. This invention also relates to novel methods for modulating bladder tissues utilizing compounds, which modulate the KCNQ family of potassium or M channels, particularly compounds which open or agonize the channels. The methods of this invention include the treatment, prevention, inhibition and amelioration of urge urinary incontinence also known as bladder instability, neurogenic bladder, voiding dysfunction, hyperactive bladder, hyperreflexic bladder, or detrusor overactivity. The methods of this invention also include the prevention and treatment of mixed stress and urge urinary incontinence, including that associated with secondary conditions such as prostate hypertrophy.

BACKGROUND OF THE INVENTION

Transmembrane currents play a fundamental role in the activation and functioning of excitable tissues. In urinary bladder smooth muscle, depolarization, excitation-contraction, and repolarization are dependent upon the activation of transmembrane currents through voltage dependent ion channels. The current underlying repolarization in detrusor smooth muscle is carried through several ion channels, virtually all of which utilize potassium as the charge carrier. These include a transient, 4-aminopyridine sensitive current (Fujii K, Foster C D, Brading A F and Parekh A B. Potassium channel blockers and the effects of cromakalim on the smooth muscle of the guinea-pig bladder. *Br J Pharmacol* 99: 779–785, 1990), a delayed rectifier (Klöckner, U. and Isenberg, G. Calcium currents of cesium loaded isolated smooth muscle cells (urinary bladder of the guinea pig). *Pflügers Arch* 405: 340–348, 1985), an ATP-dependent current (Bonev A D and Nelson M T. ATP-sensitive potassium channels in smooth muscle cells from guinea pig urinary bladder. *Am J Physiol* 264(Cell Physiol 33): C1190–C1200, 1993; Trivedi S, Stetz S L, Potter-Lee L, McConville M, Li J H, Empfield J, Ohnmacht C J, Russell K, Brown F J, Trainor D A et al. K-channel opening activity of ZD6169 and its analogs: effect on 86Rb efflux and 3H-P1075 binding in bladder smooth muscle. *Pharmacol* 50: 388–397, 1994) and a charybdotoxin-sensitive current consistent with the large-conductance, calcium-dependent potassium current (BKCa) (Zografos P, Li J H and Kau S T. Comparison of the in vitro effects of $K^+$ channel modulators on detrusor and portal vein strips from guinea pigs. *Pharmacol* 45: 216–230, 1992). Several of these channels have been the target of compounds and drugs aimed at modulating the physiology and functioning of smooth muscle and other tissues (Edwards, G. and Weston, A. H.: Pharmacology of the potassium channel openers. *Cardiovasc Drugs and Ther* 9: 185–193, 1995).

It has been suggested (Foster D C and Brading A F. The effect of potassium channel antagonists on the BRL 34915 activated potassium channel in guinea-pig bladder. *Br J Pharmacol* 92: 751, 1987) that a potassium channel opener (KCO) may be useful in the treatment of detrusor hyperactivity. An increase in potassium channel permeability would hyperpolarize the cell, bring the membrane potential further from the threshold for activation of calcium channels and reduce excitability (Brading A F. Ion channels and control of contractile activity in urinary bladder smooth muscle. *Jap J Pharmacol* 58 Suppl 2: 120P–127P, 1992). A number of potassium channel openers have shown activity in isolated tissues (Fujii et al., 1990; Malmgren A, Andersson K E, Andersson P O, Fovaeus M and Sjogren C. Effects of cromakalim (BRL 34915) and pinacidil on normal and hypertrophied rat detrusor in vitro. *J Urol* 143: 828–834, 1990; Grant T L and Zuzack J S. Effects of $K^+$ channel blockers and cromakalim (BRL 34915) on the mechanical activity of guinea pig detrusor smooth muscle. *J Pharmacol Exp Thera* 269(3): 1158–1164, 1991) and efficacy in both experimental (Foster and Brading, 1987; Malmgren A, Andersson K E, Sjogren C and Andersson P O. Effects of pinacidil and cromakalim (BRL 34915) on bladder function in rats with detrusor instability. *J Urol* 142: 1134–1138, 1989; Wojdan A, Freeden C, Woods M, Norton W. Warga D, Spinelli W, Colatsky T, Antane M, Antane S, Butera J and Argentieri T M. Comparison of the potassium channel openers ZD6169, celikalim and WAY-133537 on isolated bladder tissue and in vivo bladder instability in the rat. *J Pharmacol Exp Therap* 289: 1410–1418, 1999) and clinical bladder instability (Nurse et al., 1991). However, because these compounds also activate channels in vascular smooth muscle (causing vasodilation), the clinical utility has been severely limited by hemodynamic side effects including hypotension and tachycardia.

It has been stated previously that retigabine (N-[2-amino-4-(4-fluorobenzylamino)-phenyl]carbamic acid ethyl ester) activates a member of the KCNQ family of potassium channel in the bladder which is most likely KCNQ2/3 and/or KCNQ3/5. (Wickenden A. D., Yu, W., Zou, A., Jegla, T., & Wagoner, P. K. Retigabine, a novel anti-convulsant, enhances activation of KCNQ2/Q3 potassium channels. *Molec Pharmacol* 58: 591–600 (2000); Wickenden, A. D., Zou, A., Wagoner, P. K., & Jela, T. Characterization of the KCNQ5/Q3 potassium channels expressed in mammalian cells. *Br J Pharmacol* 132: 381–384 (2001); Rundfeldt, C., Netzer, R. The novel anticonvulsant retigabine activates M-currents in Chinese hamster ovary-cells tranfected with human KCNQ2/3 subunits. *Neuroscience Letters* 282: 73–76 (2000); Main, M. J., Cryan, J. E., Dupere, J. R. B., Cox, B., Clare, J. J. & Burbidge, S. A. Modulation of KCNQ2/3 potassium channels by the novel anticonvulsant retigabine. *Molec Pharm* 58: 253–262 (2000)). The result is an inhibition of bladder smooth muscle contractility. In addition, recent data provides evidence for the existence of the KCNQ4 channel in human bladder smooth muscle.

Current knowledge of KCNQ4 suggests that it may form a functional ion channel on its own (Søgaard S, Ljungstrøm T, Perersen K A, Olesen S P, Jensen, B S. KCNQ4 channels expressed in mammalian cells: functional characteristics and pharmacology. *Am J Physiol* 280: C859–C866, 2001), or that it may combine with KCNQ3 (Kubisch C. Schroeder B C. Friedrich T. Lutjohann B. El-Amraoui A. Marlin S. Petit C. Jentsch T J. KCNQ4, a novel potassium channel expressed in sensory outer hair cells, is mutated in dominant deafness. *Cell* 96(3):437–446, 1999). It is likely therefore, that retigabine's effects on bladder smooth muscle include activation of the KCNQ4 channel in addition to the channels formed by KCNQ2/3 and KCNQ3/5. Activation of this channel will hyperpolarize the bladder smooth muscle cells and, in doing so, relax the bladder. Since these KCNQ channels are not present in the cardiovascular system, retigabine and other molecules that activate these channels should be useful in the treatment of bladder instability without hemodynamic compromise.

M-currents have been shown to play an important functional role as determinants of cell excitability. Recent evidence indicates that the KCNQ potassium channel subunit form the molecular basis for M-current activity in a variety of tissues. From their initial report in peripheral sympathetic neurons the gene family has evolved to contain at least five major sub-units designated KCNQ1 though KCNQ5 (see reviews in Rogowski, M. A. KCNQ2/KCNQ3 $K^+$ channels and the molecular pathogenesis of epilepsy: implications for therapy. TINS 23: 393–398, (2000); Jentsch, T. J. Neuronal KCNQ potassium channels: physiology and role in disease, *Nature Rev*, (2000)). These sub-units have been shown to co-assemble to form both heteromeric and homomeric functional ion channels. Recent reports indicate that both KCNQ2 and KCNQ5 can co-assemble with KCNQ3 (Tinel, N., Lauritzen, I., Chouabe, C., Lazdunski, M., Borsotto, M. The KCNQ2 potassium channel: splice variants, functional and developmental expression. Brain localization and comparison with KCNQ3. *FEBS Letters*. 438: 171–176 (1998); Yang, W., P., Levesque, P., C., Little, W., A., Conder, M., L., Ramakrishnan, P., Neubauer, M., G., Blanar, M., A. Functional expression of two KvLQT1-related potassium channels responsible for an inherited idiopathic epilepsy. *J Biological Chemistry*. 273:19419–19423 (1998); Wang, H. S., Pan, Z., Shi, W., Brown, B. S., Wymore, R. S., Cohen, I. S., Dixon, J. E. & McKinnon, D. KCNQ2 and KCNQ3 potassium channel subunits: molecular correlets of the M-channel. *Science* 282: 1890–1893, (1998); Lerche, C., Scherer, C. R., Seebohm, G., Derst, C., Wei, A. D., Busch, A. E., Steinmeyer, K. *J Biologic Chem* (2000); Schroeder, B., C., Hechenberger, M., Weinreich, F., Kubisch, C., Jentsch, T., J. KCNQ5, a novel potassium channel broadly expressed in brain, mediates M-type currents. [Journal Article] *J Biological Chemistry*. 275: 24089–24095 (2000)) to form a functional M-channel activatable by retigabine (Wickenden A. D., Yu, W., Zou, A., Jegla, T., & Wagoner, P. K. Retigabine, a novel anti-convulsant, enhances activation of KCNQ2/Q3 potassium channels. *Molec Pharmacol* 58: 591–600 (2000); Wickenden, A. D., Zou, A., Wagoner, P. K., & Jela, T. Characterization of the KCNQ5/Q3 potassium channels expressed in mammalian cells. *Br J Pharmacol* 132: 381–384 (2001); Rundfeldt, C., Netzer, R. The novel anti-convulsant retigabine activates M-currents in Chinese hamster ovary-cells transfected with human KCNQ2/3 subunits. *Neuroscience Letters* 282: 73–76 (2000); Main, M. J., Cryan, J. E., Dupere, J. R. B., Cox, B., Clare, J. J. & Burbidge, S. A. Modulation of KCNQ2/3 potassium channels by the novel anticonvulsant retigabine. *Molec Pharm* 58: 253–262 (2000)) and blocked by either acetylcholine (Adams, P., R., Brown, D., A., Constanti, A. M-currents and other potassium currents in bullfrog sympathetic neurones. *J Physiology* 330: 537–72(1982); Brown, D., A., Adams, P., R. Muscarinic suppression of a novel voltage-sensitive K+ current in a vertebrate neurone. *Nature* 283: 673–676(1980); Shapiro, M., S., Roche, J., P., Kaftan, E., J., Cruzblanca, H., Mackie, K., Hille, B. Reconstitution of muscarinic modulation of the KCNQ2/KCNQ3 K(+) channels that underlie the neuronal M current. *J Neuroscience* 20: 1710–1721 (2000)) linopirdine or XE-991 (10,10-bis(4-pyridinylmethyl)-9 (10H)-anthracenone (Aiken, S. P., Lamp, B. J. Murphy, P. A. & Brown B. S. Reduction of spike frequency adaptation and blockade of M-current in rat CA1 pyramidal neurons by linopirdine (DuP 996) a neurotransmitter release enhancer. *Br J Pharm* 115: 1163–1168, (1995); Zaczek R. Chorvat R J. Saye J A. Pierdomenico M E. Maciag C M. Logue A R. Fisher B N. Rominger D H. Earl R A. Two new potent neurotransmitter release enhancers, 10,10-bis(4-pyridinylmethyl)-9(10H)-anthracenone and 10,10-bis(2-fluoro-4-pyridinylmethyl)-9(10H)-anthracenone: comparison to linopirdine. *J Pharmacology & Exp Therap* 285: 724–730 (1998). The parasympathetic neurotransmitter acetylcholine (Ach) is known to produce several physiological responses in bladder smooth muscle. The net result of Ach exposure is a contraction of the smooth muscle mainly through the mobilization of transmembrane and intracellular calcium stores (Hashitani H. Bramich N J. Hirst G D. Mechanisms of excitatory neuromuscular transmission in the guinea-pig urinary bladder. *Journal of Physiology* 524: 565–579 (2000)). The role that Ach plays in modulating the cell transmembrane potential, however, is more complex. Pathways for both hyperpolarization and depolarization are present with muscarinic stimulation of bladder smooth muscle. Hyperpolarization may be associated with a mechanism that involves calcium sparks and activation of calcium-dependent potassium currents (Herrera G M. Heppner T J. Nelson M T. Voltage dependence of the coupling of Ca(2+) sparks to BK(Ca) channels in urinary bladder smooth muscle. *American Journal of Physiology—Cell Physiology* 280: C481–490 (2001)).

Furthermore, there is a need to develop methods of selecting compounds useful in the treatment bladder instability and related urologic or bladder conditions. The present invention meets this need and includes methods of treatment of bladder instability and related urologic and bladder conditions.

SUMMARY OF THE INVENTION

The present invention provides a method of selecting compounds for the treatment of bladder instability comprising, expressing a target KCNQ protein in a host cell and detecting activation of said target KCNQ protein. In one embodiment, a target KCNQ protein is expressed or overexpressed naturally in a host cell or host line. In another embodiment of the present invention, a target KCNQ protein is expressed recombinantly in a host cell.

The present invention provides a method of selecting compounds for the treatment of bladder instability comprising, expressing a target KCNQ protein in a host cell and detecting activation of said target KCNQ protein, wherein said detection is performed by measuring the membrane potential of the host cell in the presence or absence of a substance; and selecting those compounds whose presence causes a change in membrane potential of the host cell.

The present invention provides a method of selecting compounds for the treatment of bladder instability comprising, expressing a target KCNQ protein in a host cell and detecting activation of said target KCNQ protein, wherein said detection is performed by fluorescence techniques with the host cell in the presence or absence of a substance; and selecting those compounds whose presence causes a hyperpolarization of said host cell as evidenced by the presence of fluorescence.

The invention also provides for this method, wherein the compounds selected exhibit the following characteristics: at least 2 times greater activity with respect to target KCNQ proteins in bladder smooth muscle compared with KCNQ proteins in other tissue; at least 2 times greater activity with respect to target KCNQ proteins in bladder smooth muscle compared with non-target KCNQ proteins; or at least 2 times greater activity with respect to target KCNQ proteins in bladder smooth muscle compared with other potassium channels. For the various embodiments of this invention, one may also select compounds that do not cross the blood brain barrier. Some compounds, which leak across the blood brain barrier, may be used as long as they exhibit no undesirable side effects. The latter is not preferred.

The present invention also provides a method of selecting a compound comprising, selecting compounds that do not cross the blood brain barrier; testing those compounds for the ability to activate a target KCNQ protein in bladder smooth muscle; selecting those compounds which show a greater ability to activate a target KCNQ protein in bladder smooth muscle when compared with activation of target KCNQ proteins in other tissue; activation of non-target KCNQ proteins, or activation of other potassium channels.

The present invention also provides a method of treatment of bladder instability by selectively activating target KCNQ channels in bladder smooth muscle, comprising administering a compound to an animal, wherein said compound selectively activates a target KCNQ protein in bladder smooth muscle.

This invention comprises methods for modulating urinary bladder tissues in a mammal, particularly including uses thereof for maintaining urinary bladder control, the methods comprising administering to a mammal in need thereof a pharmaceutically effective amount of a compound which acts as an agonist or opener of the KCNQ family of potassium channels, including the KCNQ1, KCNQ2, KCNQ3, KCNQ4, and KCNQ5 potassium channels, alone or in combination. A particular embodiment of this invention includes use in the methods described herein of one or more agonists or openers of KCNQ2/3 potassium channels. Another series of methods of this invention comprises use of one or more agonists or openers of KCNQ3/5 potassium channels. Yet another series of methods of this invention comprises use of one or more agonists or openers of KCNQ4 potassium channels.

BRIEF DESCRIPTION OF THE DRAWINGS

FIG. 4b. depicts 2 cystometrograms showing spontaneous contractions during bladder filling. Retigabine (0.1 mg/kg) (first cystometogram) significantly reduced the frequency of spontaneous contractions in comparison to the control.

DEFINITIONS

Figure 1:
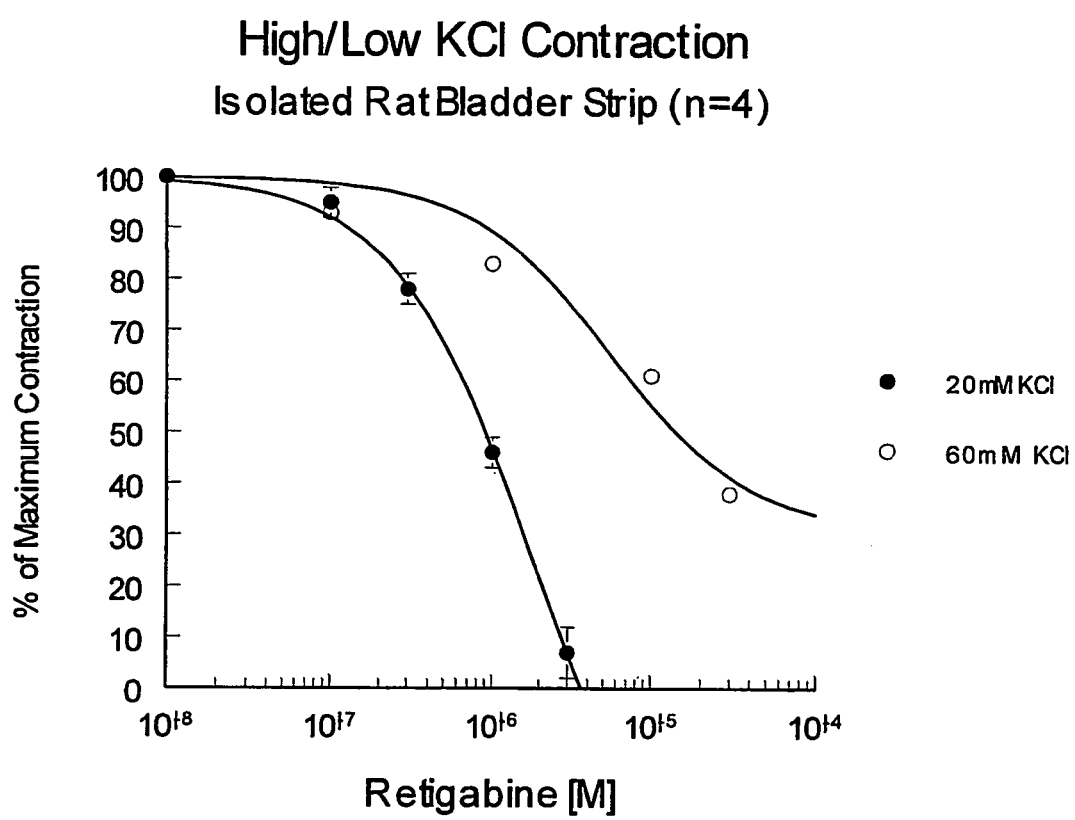
FIG. 1. is a graph depicting Retigabine concentration response curve for inhibition of isolated rat bladder strip contractions. Closed circled represent data from preparations contracted with 20 mM KCl; $IC_{50}$ was 1.4±0.1 µM. Open circles represent data from preparations contracted with 60 mM KCl; the $IC_{50}$ was 21.8±0.8 µM. This profile is consistent with a potassium channel opening mechanism where higher concentrations of KCl diminish the driving force for potassium and inhibit the potency of potassium channel openers FIG. 2. A graph of KCNQ gene expression levels in (a) human urinary bladders and in (b) rat urinary bladders measured as KCNQ mRNA/GADPH mRNA.

A KCNQ subunit is a KCNQ whole protein that forms part of a potassium channel known as the α-subunit.

A KCNQ channel is a potassium channel tetramer composed of at least one KCNQ subunit type (i.e., KCNQ1, KCNQ2, KCNQ3, KCNQ4, or KCNQ5).

A KCNQ protein is any protein of the KCNQ family, proteins predominantly involved in M-channel or potassium channel regulation. These proteins include, but are not limited to the following types: KCNQ1 (SEQ ID NO:1), KCNQ2 (SEQ ID NO:2), KCNQ3 (SEQ ID NO:3), KCNQ4 (SEQ ID NO:4), KCNQ5 (SEQ ID NO:5), KCNQ2/3, and KCNQ3/5, or any combination thereof.

A "target KCNQ protein" is a KCNQ protein occurring in the bladder smooth muscle. Preferably, it is a protein which appears at greater concentrations in the bladder smooth muscle than in other tissue. By way of example and in no way intended to limit, a "target KCNQ protein" is KCNQ3/5 or KCNQ4.

A "non-target KCNQ protein" is a KCNQ protein not occurring in bladder smooth muscle.

"Other potassium channels" are all potassium channels not composed of at least one KCNQ subunit.

DETAILED DESCRIPTION OF THE INVENTION

The present invention provides a method of selecting compounds for the treatment of bladder instability comprising, expressing a target KCNQ protein in a host cell and detecting activation of said target KCNQ protein. In one embodiment, a target KCNQ protein is expressed or overexpressed naturally in a host cell or host line. In another embodiment of the present invention, a target KCNQ protein is expressed recombinantly in a host cell.

The present invention provides a method of selecting compounds for the treatment of bladder instability comprising, expressing a target KCNQ protein in a host cell and detecting activation of said target KCNQ protein, wherein said detection is performed by measuring the membrane potential of the host cell in the presence or absence of a substance; and selecting those compounds whose presence causes a change in membrane potential of the host cell.

The present invention provides a method of selecting compounds for the treatment of bladder instability comprising, expressing a target KCNQ protein in a host cell and detecting activation of said target KCNQ protein, wherein said detection is performed by fluorescence techniques with the host cell in the presence or absence of a substance; and selecting those compounds whose presence causes a hyperpolarization of said host cell as evidenced by the presence of fluorescence.

In one embodiment, the host cell is an animal cell. In a further embodiment, the host cell is mammalian. In a further embodiment, the host cell is human. In a further embodiment, the host cell is human kidney. In a further embodiment, the host cell is human embryonic kidney. In a further embodiment, the host cell is HEK293. In an alternative embodiment, the host cell is COS.

In the present invention, compound selection is based upon detection of target KCNQ protein or KCNQ channel activation measured by various conventional means, including electrophysiological techniques (i.e., current clamping and voltage clamping). In one embodiment, membrane potential is measured using fluorescence methods. In another embodiment, membrane current is measured using voltage clamp methods. In yet another embodiment, membrane voltage is measured using current clamp techniques.

In one embodiment, substances are further selected based upon their ability to cause greater activation in target KCNQ proteins in the bladder smooth muscle than in target KCNQ proteins in other tissue. Preferably, substances are selected which cause at least 2 times greater activity in target KCNQ proteins in the bladder smooth muscle than in target KCNQ proteins in other tissue. More preferably, substances are selected which cause at least 10 times greater activity in target KCNQ proteins in bladder smooth muscle than in target KCNQ proteins in other tissue. Alternatively, substances are selected which cause at least 20, 30, 40, 50, 60, 70, 80, or 90 times greater activity in target KCNQ proteins in bladder smooth muscle than in target KCNQ proteins in other tissue. Most preferably, substances are selected which cause at least 100 times greater activity in target KCNQ proteins in bladder smooth muscle than in target KCNQ proteins in other tissue.

In another embodiment, substances are further selected based upon their ability to cause greater activation in target KCNQ proteins in bladder smooth muscle than on non-target KCNQ proteins. Preferably, substances are selected which cause at least 2 times greater activity in target KCNQ proteins in bladder smooth muscle than in non-target KCNQ proteins. More preferably, substances are selected which cause at least 10 times greater activity in target KCNQ proteins in the bladder smooth muscle than in non-target KCNQ proteins. Alternatively, substances are selected which cause at least 20, 30, 40, 50, 60, 70, 80, or 90 times greater activity in target KCNQ proteins in the bladder smooth muscle than in non-target KCNQ proteins. Most preferably, substances are selected which cause at least 100 times greater activity in target KCNQ proteins in bladder smooth muscle than on non-target KCNQ proteins.

In another embodiment, substances are further selected based upon their ability to cause greater activation in target KCNQ proteins than in other potassium channels. Preferably, substances are selected which cause at least 2 times greater activity in target KCNQ proteins in bladder smooth muscle than in other potassium channels. More preferably, substances are selected which cause at least 10 times greater activity in target KCNQ proteins in bladder smooth muscle than in other potassium channels. Alternatively, substances are selected which cause at least 20, 30, 40, 50, 60, 70, 80, or 90 times greater activity in target KCNQ proteins than in other potassium channels. Most preferably, substances are selected which cause 100 times greater activity in target KCNQ proteins than in other potassium channels.

For the various embodiments of the present invention, any one of a variety of compounds selected through the as a result of an increase in activity of a target KCNQ protein or channel is further analyzed by in vivo or in vitro analysis to detect correlation with an improvement in treatment of bladder instability or a variety of related bladder conditions as described herein.

The present invention also provides for a method of selecting a compound, comprising selecting those compounds, which substantially do not cross the blood-brain barrier or which leak across the blood brain barrier without causing undesirable side effects; testing those compounds for the ability to modulate a target KCNQ protein in bladder smooth muscle; and selecting those compounds that show a greater ability to activate a target KCNQ protein in bladder smooth muscle than to activate target KCNQ proteins in other tissue.

Known methods for predicting blood brain barrier penetration include computational methods using mathematical tools, cell culture methods using endothelial cell cultures from animal origin, high performance liquid chromotography (HPLC) using immobilized artificial membrane columns, measurement of surface activity using critical micelle concentration methodology, microdialysis techniques involving sampling tissue from the brain of a living animal for external HPLC analysis, the use of postmortem human brain capillaries, and in vivo animal studies. (Clark, D. E.; Pickett, S. Computational Methods for the Prediction of 'Drug-likeness'. *Drug Discovery Today* 5(2): 49–58, 2000; Eddy, E. P.; Maleef, B. E., Hart, T. K., Smith, P. L. In Vitro Models to Predict Blood-Brain Barrier Permeability. *Adv Drug Delivery Rev* 23: 185–1981, 1997; Gumbleton, M. and Kenneth L. Audus. Progress and Limitations in the Use of In Vitro Cell Cultures to Serve as a Permeability Screen for the Blood-Brain Barrier. *J Pharm Sci* 90: 1681–1698, 2001).

The present invention also provides for a method of treatment for bladder instability comprising administering to an animal, preferably a mammal or a human, a compound that selectively activates a target KCNQ protein in bladder smooth muscle.

The methods of this invention are useful for inducing, assisting or maintaining desirable bladder control in a mammal experiencing or susceptible to bladder instability or urinary incontinence. These methods include prevention, treatment or inhibition of bladder-related urinary conditions and bladder instability, including nocturnal enuresis, nocturia, voiding dysfunction and urinary incontinence. Also treatable or preventable with the methods of this invention is bladder instability secondary to prostate hypertrophy. The compounds described herein are also useful in promoting the temporary delay of urination whenever desirable. The compounds of this invention may also be utilized to stabilize the bladder and treat or prevent incontinence, including urge urinary incontinence or a combination of urge and stress incontinence in a mammal, which may also be referred to as mixed urge and stress incontinence. These methods include assistance in preventing or treating urinary incontinence associated with secondary conditions such as prostate hypertrophy.

These methods may be utilized to allow a recipient to control the urgency and frequency of urination. The methods of this invention include the treatment, prevention, inhibition and amelioration of urge urinary incontinence also known as bladder instability, neurogenic bladder, voiding dysfunction, hyperactive bladder, detrusor overactivity, detrusor hyper-reflexia or uninhibited bladder.

As described above, methods of this invention include treatments, prevention, inhibition or amelioration of hyperactive or unstable bladder, neurogenic bladder or hyperreflexic bladder. These uses include, but are not limited to, those for bladder activities and instabilities in which the urinary urgency is associated with prostatitis, prostatic hypertrophy, interstitial cystitis, urinary tract infections or vaginitis. The methods of this invention may also be used to assist in inhibition or correction of the conditions of Frequency-Urgency Syndrome.

The methods of this invention may also be used to treat, prevent, inhibit, or limit the urinary incontinence, urinary instability or urinary urgency associated with or resulting from administrations of other medications.

The methods of this invention are useful for inducing or assisting in urinary bladder control or preventing or treating the maladies described herein in humans in need of such relief, including adult and pediatric uses. However, they may also be utilized for veterinary applications, particularly including canine and feline bladder control methods. If desired, the methods herein may also be used with farm animals, such as ovine, bovine, porcine and equine breeds.

The applications may utilize conventional oral, rectal, parenteral or intravenous delivery methods as conventionally utilized in veterinary practice. Most preferable in most instance for home use with companion animals are oral tablets or capsules or neat compound or powdered or granular pharmaceutical formulations which may be mixed with chewable or liquid veterinary formulations or food materials or liquids acceptable to the animal in question.

As used herein, the terms "pharmaceutically effective amount" or "therapeutically effective amount" mean the total amount of each active component of the pharmaceutical composition or method that is sufficient to show a meaningful patient benefit, i.e., treatment, prevention or amelioration of urinary incontinence or the excessive or undesirable urge to urinate, or a decrease in the frequency of incidence of urinary incontinence. When applied to an individual active ingredient, administered alone, the term refers to that ingredient alone. When applied to a combination, the term refers to combined amounts of the active ingredients that result in the therapeutic effect, whether administered in combination, serially or simultaneously.

The examples described below are for illustrative purposes, and the present invention is not meant to be limited to these examples.

In one embodiment, the present invention involves a high throughput screening of compounds and selection of lead compounds by indirectly measuring the membrane potential of transfected cells as described in more detail below.

EXAMPLE 1

High Throughput Screening

Mammalian (e.g., HEK-293, COS) cells are transfected (either stable or transient) with cDNA or cRNA for KCNQ potassium channels. These cells express and incorporate functional KCNQ channels in their membrane that modulate membrane potential. Several methods are available to monitor transmembrane potential. One such method employs the use of a Fluorescence Imaging Plate Reader (FLIPR), and voltage-sensitive fluorescent dyes. Transfected cells are grown on the well bottoms e.g., of a 96 or 384 well plate. The instrument has the capability of pipetting into and recording fluorescent signals from all wells simultaneously. In this way, large numbers of compounds can be tested rapidly for their ability to modulate the KCNQ-dependent transmembrane potential. Compounds, which cause hyperpolarization of the transfected cell membrane, are further analyzed through various techniques. In one example, the fluorescence imaging plate reader (FLIPR) uses bis-oxonol (DiBAC4) as the voltage sensitive fluorescent probe.

In one embodiment, following, high throughput screening, secondary analysis of compounds selected via FLIPR is performed in order to obtain functional data for lead compounds. In particular, secondary analysis is performed as described more fully below.

EXAMPLE 2

In Vitro (Activity) Assays—Secondary Analysis

Isolated Rat Bladder Strip

Male Sprague-Dawley rats (200–400 grams) are euthanized by CO2 inhalation and exsanguination. Their urinary bladders are rapidly removed and placed in 370° C. physiological salt solution (PSS) that contained the following (mM): NaCl (118.4), KCl (5), $CaCl_2$ (2.5), $MgSO_4$ (1.2), $KH_2PO_4$ (1.2), $NaHCO_3$ (24.9) and D-glucose (11.1) gassed with $O_{2/CO2}$ (95% /5%) to achieve a pH of 7.4. The dome of the bladder is isolated from the trigon region and this tissue is then cut into 4–5 mm wide by 10 mm long strips. One end is secured to the bottom of a water jacketed tissue bath and the other to a GRASS isometric force transducer (Grass Instruments, Quincy, Mass.). Tissues are pretensioned (0.25 to 0.5 grams), and after 30 minutes of equilibration are contracted with an additional 15 mM KCl (total of 20 mM) and again allowed to equilibrate until the preparations are contracting steadily. Any of a variety of compounds are administered directly into the tissue baths as sequential concentrations. Transducer signals are digitized (12 bit resolution) and analyzed on-line using a 586-based computer and custom software. The area under the contraction curve (AUC) is used as a measure of contractility since the spontaneous bladder contractions are irregular in amplitude and frequency. A 5-minute AUC value is taken 30 minutes after administration of each compound concentration to the tissue bath.

Isolation of Rat Detrusor Cells

Rat detrusor cells are isolated in a manner previously described for guinea-pig detrusor (Sheldon J H, Norton N W and Argentieri T M (1997) Inhibition of guinea pig detrusor contraction by NS-1619 is associated with activation of BKCa and inhibition of calcium currents. *J Pharmacol Exp Thera* 283(3): 1193–1200). Male Sprague-Dawley rats (Charles River, Wilmington, Mass.; 200–400 grams) are euthanized by $CO_2$ inhalation and exsanguination. Their urinary bladders are rapidly removed and placed in 37° C. physiological solution with the following composition (mM): Na glutamate (80.0), NaCl (54.7), KCl (5.0), NaHCO$_3$ (25.0), MgCl$_2$.2H$_2$O (2.5), D-glucose (11.8) and CaCl$_2$ (0.2) gassed with O$_2$—CO$_2$, 95%/5% for a final pH of 7.4. The dome of the bladder is isolated from the trigone region and the mucosa is removed. This tissue is then cut into 2–3 mm wide strips and placed into fresh buffer for 1 hour. Tissues are then transferred into 10 ml of an isolation buffer containing the above composition plus collagenase type VIII (1.0 mg/ml) and pronase (0.25 mg/ml). After 10 minutes the isolation buffer is replaced with fresh isolation buffer for an additional 10 min. The tissue is then washed 3 times in fresh collagenase and pronase free solution and stored at room temperature until studied. Cells for study are prepared by triturating 1–2 pieces of detrusor tissue in 2 ml of fresh isolation buffer for 5 minutes with a polished Pasteur pipette, (tip diameter ~1.5 mm) attached to a modified Harvard Respirator pump (Harvard Apparatus, Southnatic, Mass.) at a rate of 20×/min. with an approximate volume of 5 ml. Cells are then placed on a microscope stage in a temperature regulated tissue bath at 32.5° C. and continually superfused with PSS.

Cell Electrophysiology

Single cell recordings are performed with a List-Medical EPC-7 patch clamp amplifier (Adams & List Assoc., Westbury, N.Y.). Pipette electrodes had tip resistances of 2–4 MΩ and are filled with the following composition (mM): KCl (126.0), MgCl$_2$.6H$_2$O (4.5), ATP Mg salt (4.0), GTP tris salt (0.3), creatine PO$_4$ (14.0), D-glucose (9.0), EGTA (9.0), HEPES (9.0). The pH is adjusted to 7.4 with KOH. Signals are acquired (3 kHz high frequency cut-off, 12 bit resolution) using a 586-based personal computer.

To validate, changes in membrane potential observed indirectly via FLIPR, voltage and current clamp analysis are performed as described.

EXAMPLE 3

Current Clamp Recordings

Cell resting membrane potential (RMP) is measured in current clamp using the above mentioned instrumentation and pipette solutions. For these experiments nystatin is also added to the pipette solution (100 μg/ml) to allow recording through utilization of the perforated patch technique (Korn, et al, 1991). After stable access is achieved, RMP is recorded for a 5 minute control period followed by 5 minute of drug application (0.3 and 1.0 μM). After this time, various antagonists (linopirdine, XE-991) are added to the perfusate and RMP is recorded for an additional 5 minutes.

Voltage Clamp Recordings

Whole cell recordings are made using broken patch access. Currents are evoked using either voltage steps (Vh=−50; Vt=−60 to 40 mV) or voltage ramps (−60 to 40 mV at 3.3 mV/sec.). The exact voltage clamp protocols are well known in the art. After stability is achieved control currents are recorded. Next, test compound is added to the superfusate. Currents are recorded for 5 to 10 minutes or until compound effects reach steady state. This is followed either by washout or addition of antagonists (linopirdine, XE-991) to the superfusate.

To further verify that changes in membrane potential and membrane current are occurring as a result of activation of KCNQ potassium channels, a *Xenopus oocyte* assay is performed as follows:

EXAMPLE 4

*Xenopus Oocyte* Assay

*Xenopus laevis* are used because their ovaries always contain oocytes at different stages (stages V and VI are considered mature and used for expression purposes). These oocytes have very limited number of endogenous ion channels and receptors and can express "foreign" mRNAs easily. Therefore, in modern electrophysiology and cellular and molecular biology, expression of mRNAs in *Xenopus oocytes* has become a good tool for examining the properties of receptors and ion channels from mammalian (including human) tissues. Frogs are anesthetized in 0.3 tricaine methanesulphonate (MS222) for at least 45 min. A lateral incision (<1 cm) is made through the epidermis and the muscle fascia. The distal lobe of the ovary is pulled out using blunt, atraumatic forceps and cut. Each layer of the wound is closed separately using 4-O black monofilament nylon and FS-2 cutting needles.

After removal, oocytes are cleaned and separated by incubating with enzyme solutions. Eggs are then injected with message for KCNQ subunits. After several days the channel proteins are expressed in the oocyte membrane. Trans membrane currents and voltage can be measured using standard two microelectrode recording techniques.

Additional known, available, or conventional techniques are applied to selected compounds to obtain functional in vitro or in vivo data.

EXAMPLE 5

In Vivo (Efficacy) Assays

A) Hyperreflexic Bladders

Micturition frequency is enhanced by the stimulation of sensory afferents using a dilute acetic acid solution in the cystometric infusate as previously described by Birder and de Groat (Birder L A. de Groat W C. Increased c-fos expression in spinal neurons after irritation of the lower urinary tract in the rat. J Neuroscience 12: 4878–89, (1992)). Briefly, female Sprague-Dawley rats (190–210 g) are anesthetized with urethane (lg/kg/10 mL, i. p.; 1 g/kg/10 mL, s. q.). The trachea is cannulated with PE205 to ensure a patent airway. The external jugular is cannulated with PE50 tubing for administration of compound. The bladder is exposed through a midline incision, and an angiocatheter (24 g, TEFLON), is heat flared at the end and inserted into the dome of the bladder and secured with 4-0 silk. The bladder is flushed with normal saline and allowed to equilibrate for 1 hour before cystometry is performed. Using a "T" connector, the bladder catheter is connected to a Statham pressure transducer (Model P23Db) and to a Harvard infusion pump. Cystometric recordings are monitored on a GRASS polygraph while infusing the bladder with saline containing 0.25% acetic acid at a rate of 2.4 mL/hr. for one hour. Next, compound is administered intravenously and the cystometry monitored for an additional 2 hours. The following cystometric parameters are recorded: micturition interval, micturition amplitude, micturition threshold pressure, bladder capacity, bladder compliance and the number of spontaneous bladder contractions (SBC) during the filling phase. The control period is taken as the 30 minute time period of acetic acid saline perfusion before dosing.

B (i) Hypertrophied Bladders

The method for producing hypertrophied, unstable bladders was modified from that reported by Malmgren, et al. (Malmgren A. Sjogren C. Uvelius B. Mattiasson A. Andersson K E. Andersson P O. Cystometrical evaluation of bladder instability in rats with infravesical outflow obstruction. *J Urology* 137:1291–4, (1987)) and reported by Wojdan, et al. (Wojdan A. Freeden C. Woods M. Oshiro G. Spinelli W. Colatsky T J. Sheldon J H. Norton N W. Warga D. Antane M M. Antane S A. Butera J A. Argentieri T M. Comparison of the potassium channel openers, WAY-133537, ZD6169, and celikalim on isolated bladder tissue and in vivo bladder instability in rat. *J Pharmacol Exp Therap* 289:1410–1418, (1999)). Briefly, female Sprague-Dawley rats (190–210 g) are used. Animals are anesthetized with isoflurane. Once the animals are anesthetized, the bladder and urethra are exposed through a midline incision and a 4-0 silk ligature is tied around the proximal urethra in the presence of a stainless steel rod (1 mm diameter). When the rod is then removed, a calibrated partial occlusion of the urethra results. The abdominal muscle is closed using 3-0 silk and the skin is closed with surgical staples. Each rat receives 150,000 units of bicilin C-R, i.m. During the following 6–9 weeks, bladder hypertrophy and instability results from the partial outlet obstruction.

(ii) Catheter Implantation

Using the above animals, after approximately 6–9 weeks of resulting hypertrophy as described above, the animals are re-anesthetized with isoflurane, the ligature is removed from the proximal urethra, and a flared catheter (PE60) is placed in the dome of the bladder; secured with a suture. The catheter is exteriorized under the skin through an opening in the back of the neck. The abdominal incision is sutured, and the free end of the catheter sealed. Following surgery, animals are given a second dose of bicilin C-R (150,000 units/rat, i.m.).

(iii) Cystometric Evaluation

Two days after catheter implantation, animals are placed in a metabolic cage, and the bladder catheter is attached (using a "T" connector) to both a STRATHAM pressure transducer (Model P23Db) and to a Harvard infusion pump. Urine volume is monitored with a plastic beaker attached to a force displacement transducer (GRASS FT03). The cystometric evaluation of bladder function is started by infusing the bladder with saline (10–20 mL/hr depending upon the degree of hypertrophy). The following cystometric parameters are recorded: number of spontaneous bladder contractions (SBC) during the filling phase, micturition amplitude and micturition volume. Cystometric recordings are made on a GRASS polygraph and included at least 2 micturition intervals or 20 minutes. Next, the rats are rested for a two-hour period then orally gavaged with the test compound. A second cystometry is performed approximately 60 minutes after administration of test compound. A separate group of vehicle (saline) treated animals with hypertrophied bladders serve as time/vehicle controls.

Use of Retigabine and Other Experiments Establishing KCNQ as a Target

In this report, we show that retigabine can relax isolated KCl or carbachol-contracted rat bladder strips, and this relaxation can be reversed by either linopirdine or XE-991. Using quantitative rtPCR we have identified the expression of KCNQ1, 3 and 5 in the rat urinary bladder and KCNQ3 and 5 in cultured human bladder smooth muscle cells. The highest levels of expression were seen for KCNQ5>KCNQ1>KCNQ3 in the rat and KCNQ5>KCNQ3 in human cells. M-current activity was demonstrated by the presence of a retigabine-induced increase in repolarizing current in isolated rat and human bladder smooth muscle cells. The retigabine-dependent current and hyperpolarization was reversed by the addition of either linopirdine or XE-991, or acetylcholine to the tissue bath. Finally, bladder cystometry revealed that retigabine could inhibit spontaneous bladder contractions and micturition in a rat neurogenic bladder model in a dose-dependent manner.

At present, KCNQ derived M-current channels have mainly been identified in neuronal, cardiac (Barhanin, J., Lesage, F., Guillemare, E., Fink, M., Lazdunski, M., Romey, G., K(V)LQT1 and lsK (minK) proteins associate to form the I(Ks) cardiac potassium current. *Nature* 384: 78–80 (1996); Sanguinetti, M., C., Curran, M., E., Zou, A., Shen, J., Spector, P., S., Atkinson, D., L., Keating, M., T. Coassembly of K(V)LQT1 and minK (IsK) proteins to form cardiac I(Ks) potassium channel. *Nature* 384: 80–83 (1996)) and skeletal muscle (Schroeder, B., C., Hechenberger, M., Weinreich, F., Kubisch, C., Jentsch, T., J. KCNQ5, a novel potassium channel broadly expressed in brain, mediates M-type currents. *J Biological Chemistry* 275: 24089–24095 (2000)) tissue. A number of syndromes have been associated with defects in these proteins including: long QT syndrome and cardiac arrhythmias (KCNQ1; Sanguinetti et al), benign familial neonatal convulsions (KCNQ2 and KCNQ3 (Biervert, C., Schroeder, B., C., Kubisch, C., Berkovic, S., F., Propping, P., Jentsch, T., J., Steinlein, O., K. A potassium channel mutation in neonatal human epilepsy. *Science* 279: 403–406 (1998); Singh, N., A., Charlier, C., Stauffer, D., DuPont, B., R., Leach, R., J., Melis, R., Ronen, G., M., Bjerre, I., Quattlebaum, T., Murphy, J., V., McHarg, M., L., Gagnon, D., Rosales, T., O., Peiffer, A., Anderson, V., E., Leppert, M. A novel potassium channel gene, KCNQ2, is mutated in an inherited epilepsy of newborns. *Nature Genetics* 18: 25–29 (1998); Charlier, C., Singh, N., A., Ryan, S., G., Lewis, T., B., Reus, B., E., Leach, R., J., Leppert, M. A pore mutation in a novel KQT-like potassium channel gene in an idiopathic epilepsy family. *Nature Genetics* 18: 53–55 (1998)) and nonsyndromic autosomal dominant deafness (KCNQ4 (Kubisch, C., Schroeder, B., C., Friedrich, T., Lutjohann, B., El-Amraoui, A., Marlin, S., Petit, C., Jentsch T., J., KCNQ4, a novel potassium channel expressed in sensory outer hair cells, is mutated in dominant deafness. *Cell* 96: 437–446 (1999); Coucke, P., J., Van Hauwe, P., Kelley, P., M., Kunst, H., Schatteman, I., Van Velzen, D., Meyers, J., Ensink, R., J., Verstreken, M., Declau, F., Marres, H., Kastury, K., Bhasin, S., McGuirt, W., T., Smith, R, J., Cremers, C., W., Van de Heyning, P., Willems, P., J., Smith, S., D., Van Camp, G. Mutations in the KCNQ4 gene are responsible for autosomal dominant deafness in four DFNA2 families. *Human Molecular Genetics* 8:1321–1328 (1999)). To date, however, there have been no reports of evidence for KCNQ currents in other tissue types, including bladder smooth muscle. The data presented here provide molecular and physiological evidence for the existence of KCNQ-based M currents that contribute to membrane potential and functioning of urinary bladder smooth muscle.

We isolated rat bladder strips from male Sprague-Dawley rats as previously described, (Wojdan, A., Freeden, C., Woods, M., Oshiro, G., Spinelli, W. et al., *J Pharmacol Exp Therap* 289: 1410–1418 (1999)) and precontracted them with 20 mM KCl. The KCNQ channel agonist retigabine, was added to the tissue bath in increasing concentrations, and area under the contraction curve was analyzed. Retigabine inhibited the spontaneous contractions in a concentration-dependent manner with an $IC_{50}=1.4\pm0.1$ μM (n=4; FIG. 1). The effects of drug were not reversed by the ATP-sensitive $K^+$ channel blocker, glyburide (10 μM), but were antagonized 94.8±17.5% by 10 μM of the M-current inhibitor, linopirdine or the selective KCNQ channel blocker XE-991.

In another study, isolated rat bladder strips were precontracted with 60 mM KCl (FIG. 1). The $IC_{50}$ for inhibition of contraction under this condition was significantly greater (21.8±0.8 μM; n=4), than the $IC_{50}$ obtained with 20 mM KCl (p<0.05).

In a third set of bladder strips contracted with the muscarinic agonist carbachol (200 nM), retigabine produced a concentration-dependent inhibition of contraction with an $IC_{50}$ of 3.5±0.9 nM (n=14). The difference in $IC_{50}$s between 20 and 60 mM KCl depolarizations are consistent with a potassium channel opening mechanism. The inability of the ATP-dependent $K^+$ channel antagonist glyburide, and the ability of linopirdine or XE-991 to antagonize the effects of retigabine suggests that the bladder smooth muscle contractility is inhibited via activation of a KCNQ channel.

Figure 2:
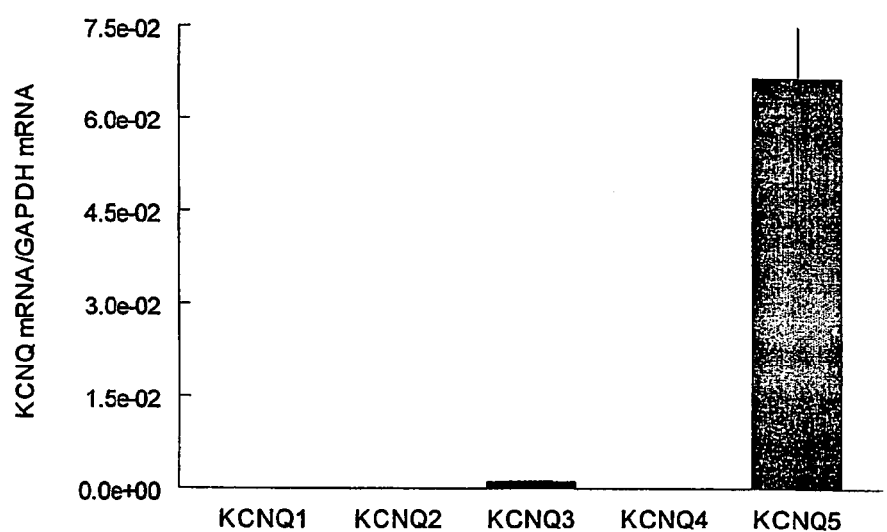
In FIG. 2a, quantitative reverse transcriptase polymerase chain reaction (rtPCR) was performed on RNA isolated from rat bladder smooth muscle. Message for KCNQ1, KCNQ3 and KCNQ5 was seen. No message for KCNQ2 or KCNQ4 was present.
In FIG. 2b, rtPCR performed on RNA isolated from cultured human bladder smooth muscle cell. Message was seen for KCNQ3 and KCNQ5
Figure 2:
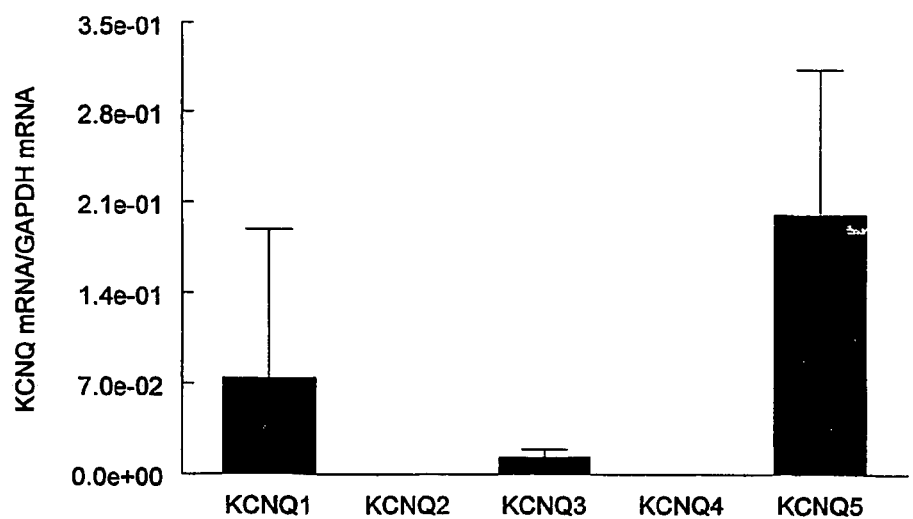

We next probed the KCNQ subunit composition in rat bladder using quantitative reverse transcriptase polymerase chain reaction (rtPCR). Data (rtPCR) are presented as percent RNA/GAPDH RNA level. The highest level of expression was seen with the KCNQ5 gene (0.2±0.1 ng KCNQ5 mRNA/GAPDH mRNA). KNCQ1 showed levels of 0.07±0.1 ng mRNA/GAPDH mRNA, while KCNQ3 was calculated at 0.01±0.01 ng mRNA/GAPDH mRNA. No signals were seen for either the KCNQ2 or KCNQ4 gene (FIG. 2b). The KCNQ subunit composition in cultured human bladder smooth muscle cells was KCNQ5 (0.07±0.0601 ng mRNA/GAPDH mRNA) and KCNQ3 (1.5×10$^{-3}$±0.1×10$^{-3}$ ng mRNA/GAPDH mRNA. There was no evidence for expression of KCNQ1, KCNQ2 or KCNQ4 in these cells.

Current data suggest that the KCNQ2 and KCNQ3 subunits form a heteromultimeric channel that can be agonized by retigabine. KCNQ3 and KCNQ5 also appear to form a functional ion channel similarly sensitive to retigabine. KCNQ4 may form a heteromultimer with KCNQ3 or a homermeric ion channel that can be activated by retigabine (Schrøder, R. L., Jespersen, T., Christophersen, P., Strøbæk, D., Jensen, B. et al. KCNQ4 channel activation by BMS-204352 and retigabine. *Neuropharmacol* 40: 888–898 (2001)). The above data provides molecular evidence for the expression of KCNQ mRNA in rat and human bladder smooth muscle. Activation of the ion channels formed by this message would be consistent with the retigabine-induced relaxation of bladder smooth muscle.

Figure 3:
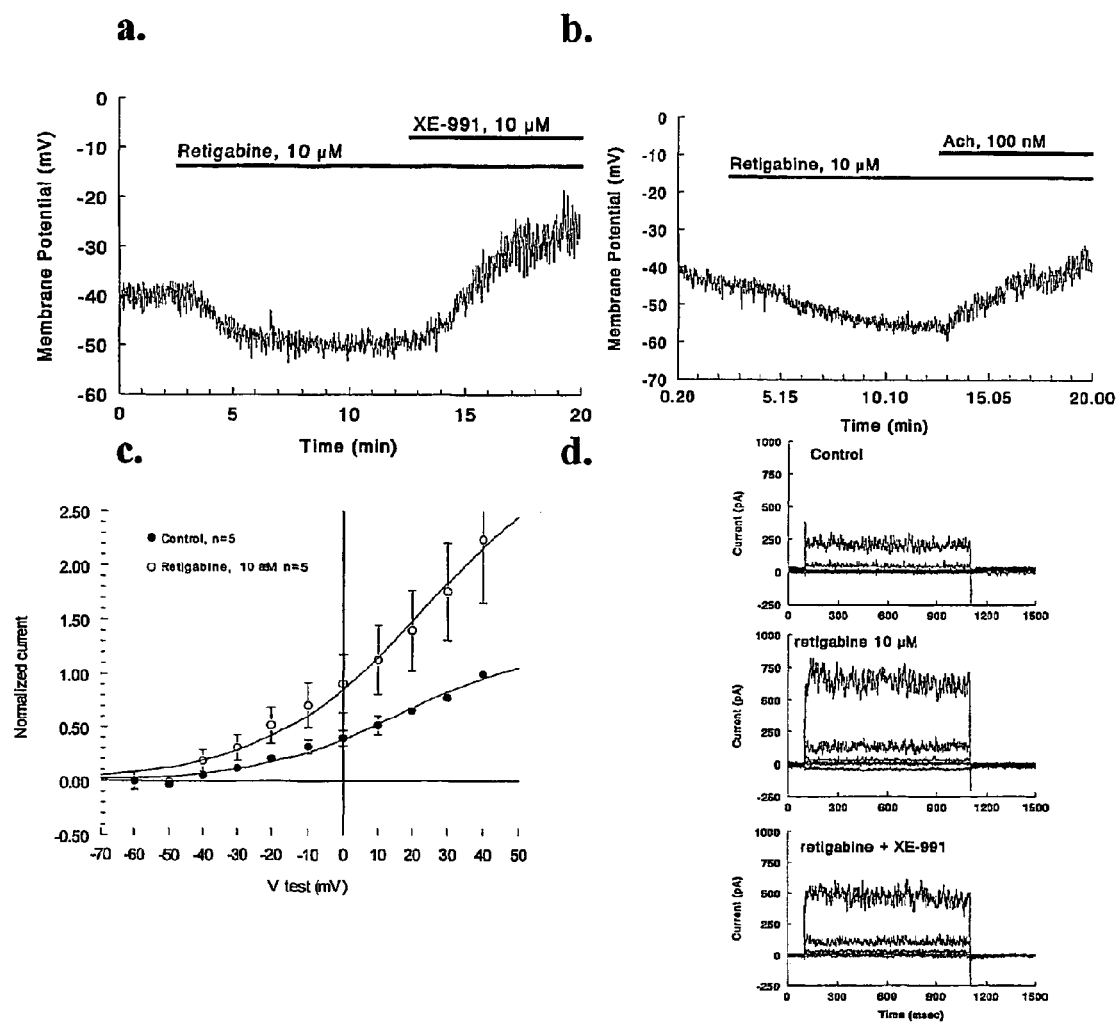
FIG. 3. a. A graph of a current clamp tracing from an isolated rat bladder smooth muscle cell. Resting membrane potential was −40 mV prior to exposure to 10 µM retigabine. Retigabine hyperpolarized the cell by approximately 10 mV. This hyperpolarization was reversed by the addition of 10 µM XE-991. b. A graph of a current clamp tracing from an isolated rat bladder smooth muscle cell showing a retigabine-induced hyperpolarization followed by a depolarization by 100 nM Ach. c. A graph of current-voltage relationship for outward current before (control) and after retigabine. d. Three graphs of voltage clamp tracings from isolated human bladder smooth muscle cell. Retigabine increased an outward current that was partially reversed by 10 µM XE-991.

Cellular electrophysiological studies were conducted using both voltage and current clamp techniques (Hammill, O., P., Marty, A., Neher, E., Sakmann, B. & Sigworth, F. J.: Improved patch-clamp techniques for high-resolution current recordings from cells and cell-free membrane patches. *Pflugers Arch* 391: 85–100 (1981)) from Sprague-Dawley rat (200–400 grams) bladders as previously described, (Wojdan, A., Freeden, C., Woods, M., Oshiro, G., Spinelli, W. et al., *J. Pharmacol Exp Therap* 289: 1410–1418 (1999)) and from a human bladder, primary cell culture (Colnetics, San Diego, Calif.). In rat cells, the average, control resting membrane potential (RMP) was −29.0±4.5 mV. After exposure to 10 μM retigabine, there was a significant (p<0.5, n=3) hyperpolarization to −43.0±3.5 mV. Hyperpolarization was completely reversed by washout or the addition of 10 μM XE-991 (FIG. 3a). Interestingly, XE-991 depolarized the cell below its initial RMP suggesting that KCNQ currents are a determinant of normal membrane potential. The retigabine-induced hyperpolarization could also be antagonized by the application of 100 nM Ach (FIG. 3b). Voltage clamp studies revealed a retigabine induced increase in outward current at test potentials between −50 and 80 mV (FIG. 3b,c; n=5). Increases in outward current were not sensitive to 100 nM iberiotoxin (Galvez, A. et al.: Purification and characterization of a unique, potent, peptidyl probe for the high conductance calcium-activated potassium channel from venom of the scorpion buthus tamulus. *J Biol Chem* 265: 11083–11090 (1990)) (IbTx), but were partially reversed by linopirdine (50 μM) or XE-991 (10 μM) (data not shown). Cultured human bladder smooth muscle cells were more depolarized with resting membrane potentials of −8.0±2.8 mV. Exposure to retigabine hyperpolarized these cells by 11±1.1 mV (n=3) and increased outward currents (FIG. 3d). These changes could be partially reversed by XE-991.

These data demonstrate the existence of an outward current in rat and human bladder smooth muscle that can be activated by the KCNQ channel opener retigabine. Activation of this current was associated with a hyperpolarization that was blocked by Ach and the KCNQ channel blockers linopirdine and XE-991. It can be concluded that the retigabine-dependent outward current in bladder smooth muscle is electrophysiologically and pharmacologically consistent with that reported for the M-current in other tissues.

Figure 4:
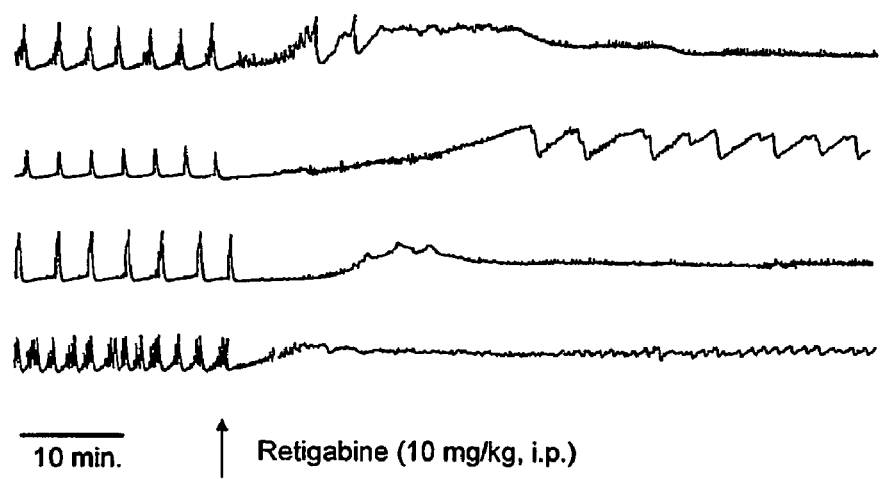
FIG. 4. a. depicts cystometrograms from four rats. Bladder infusate contained 0.25% acetic acid to induce spontaneous contractions and shorten the micturition interval. Micturition was completely blocked within minutes of dosing retigabine (10 mg/kg, i.p.).
Figure 4:
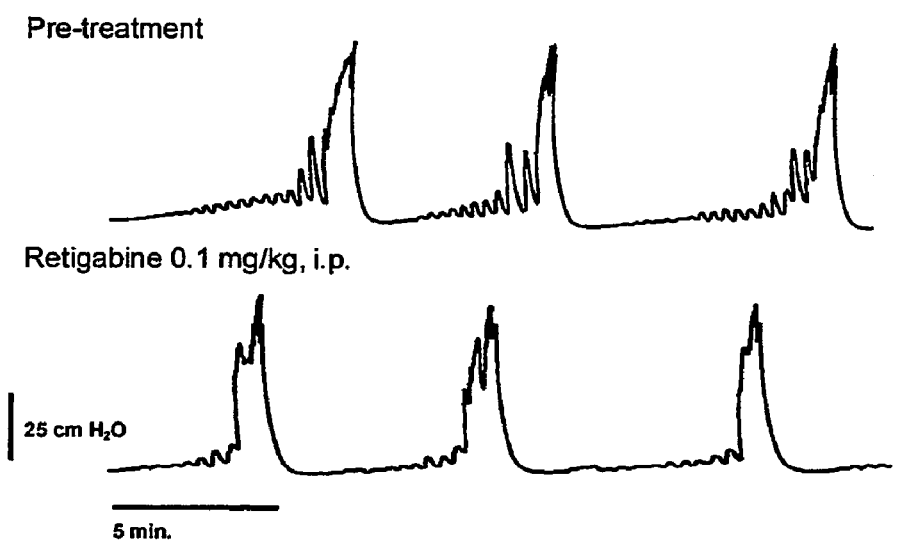

Rat bladder micturition frequency (enhanced by infusate containing 0.25% acetic acid (Birder, L. A., & deGroat, W., C. Increased c-fos expression in spinal neurons after irritation of the lower urinary tract in the rat. *J Neurosc* 12: 4878–4889 (1992))) was inhibited by retigabine in a dose-dependent (0.1–10 mg/kg, i.p.) manner. At 10 mg/kg, micturition was blocked in 100% of animals dosed; the population $ED_{50}$ was 1–2 mg/kg (n=5–8). Micturition block lasted for up to 90 minutes (FIG. 4a). Cystometrograms showed a high degree of spontaneous contractions that were sensitive to doses of retigabine that did not completely bock micturition. There was a 43.5±14.1% inhibition (p<0.05) of spontaneous contractions at 1 mg/kg, i.p. (FIG. 4b).

Summary

M-currents have been shown to play an important functional role in a variety of tissues. The gene family contains at least five major sub-units—KCNQ1 though KCNQ5. These sub-units have been shown to co-assemble to form functional heteromeric and homomeric ion channels. The only previous evidence of M-currents in smooth muscle has been that reported in toad gastric smooth muscle (Sims, S., T., Singer J., J., & Walsh, J., V. Antagonistic adrenergic-muscarinic regulation of M current in smooth muscle cells. *Science* 239: 190–193 (1988). Our data provide physiological and pharmacological support for an M-current in rat and human bladder smooth muscle, and provides molecular evidence suggesting that the KCNQ potassium channel underlies this current. We have shown that the KCNQ channel agonist, retigabine, can relax precontracted, isolated rat bladder strips. The fact that the addition of glyburide did not antagonize the relaxation suggests that retigabine does not work via activation of the ATP-dependent potassium channel. Using quantitative rtPCR we have identified the expression of mRNA for KCNQ1, 3 and 5 in the rat and KCNQ3 and 5 in human urinary bladder. Electrophysiological assessment revealed a retigabine-induced outward current and hyperpolarization that was antagonized by the M-current blocker linopirdine and KCNQ channel antagonist XE-991. These data provide evidence for a KCNQ mediated M-current that appears to be an important determinant of urinary bladder smooth muscle excitability. We believe that this channel may represent a novel molecular target for the treatment of bladder hyperactivity associated with urge urinary incontinence.

Methods

Rat bladder strips were isolated and prepared as previously described (Wojdan, A., Freeden, C., Woods, M., Oshiro, G., Spinelli, W. et al., J Pharmacol ExpTherap 289:1410–1418 (1999)). Preparations were contracted with either 20 or 60 mM KCl, or 200 nM carbachol. A five minute area under the contraction curve was acquired 20 minutes after addition of each concentration of retigabine using a 12 bit D/A and a 586 based personal computer running custom software. Message for KCNQ subunits was probed using quantitative rtPCR on an ABI PRISM 7700 Sequence Detection System (TAQMAN). Forward and reverse primers and TAQMAN probes were designed using published RNA sequences for human KCNQ1–5 and rat KCNQ 1–4 listed within the NCBI data base. Since no rat sequence for KCNQ5 were currently published, probes and primers were designed by BLAST analysis of rat Expressed Sequence Tags (EST) using the known mouse KNCQ5 sequence. From homologous EST sequences, a contiguous sequence of 384 base pairs was constructed. Probes and primers were designed against this sequence. BLAST analysis of our rat KCNQ5 probes and primer were selective for mouse and human KCNQ5 sequences. PCR products were confirmed by gel electrophoresis (data not shown). Cells for electrophysiology were prepared from rat bladder smooth muscle as previously described (Wojdan et al., 1999). Human bladder smooth muscle cells were obtained from Clonetics, San Diego, Calif. Cells were removed from culture with trypsin and added directly into the recording chamber. All recordings were made at 320 C and acquired on a 586 based personal computer using pCLAMP (Axon Instruments) software. Current clamp recordings were performed with nystatin access as previously described (Wojdan et al.). Rat bladder cystometry was performed as previously described (Woods, M., Carson, N., Norton N., W., Sheldon J., H., & Argentieri T., M., Efficacy of the beta 3-adrenergic receptor agonist CL-316243 on experimental bladder hyperreflexia and detrusor instability in the rat. Journal of Urology 166: 1142–1147 (2001)). Tracings were acquired and analyzed off-line using a POWERLAB ML795 (16 bit A/D) data acquisition system.

Publications cited herein above are incorporated by reference.

We claim:

1. A method of screening for a compound for the inhibition of urge urinary incontinence comprising:
    (a) expressing a target KCNQ protein in a host cell; and
    (b) detecting activation of said target KCNQ protein in the host cell; wherein the detection is performed by measuring the membrane potential of the host cell in the presence or absence of said compound and selecting the compound whose presence causes hyperpolarization in membrane potential of the host cell.

2. The method of claim 1, wherein the host cell is an animal cell.

3. The method of claim 1, wherein the host cell is mammalian.

4. The method of claim 1, wherein the host cell is human.

5. The method of claim 1, wherein the host cell is human embryonic kidney.

6. The method of claim 1, wherein the host cell is HEK293 or a COS cell.

7. The method of claim 1, wherein detection is performed by measuring membrane potential using an electrophysiological technique or a fluorescence technique.

8. The method of claim 1, wherein the compound exhibits at least 2 times greater activity on a target KCNQ protein in bladder smooth muscle than on another target KCNQ protein in tissue other than bladder smooth muscle.

9. The method of claim 1, wherein the compound exhibits at least 10 times greater activity on a target KCNQ protein in bladder smooth muscle than on another target KCNQ protein in tissue other than bladder smooth muscle.

10. The method of claim 1, wherein the compound exhibits at least 100 times greater activity on a target KCNQ protein in bladder smooth muscle than on another target KCNQ protein in tissue other than bladder smooth muscle.

11. The method of claim 1, wherein the compound exhibits no detectable activity on another target KCNQ protein in tissue other than bladder smooth muscle.

12. The method of claim 1, wherein the compound exhibits at least 2 times greater activity on a target KCNQ protein in bladder smooth muscle than on a non-target KCNQ protein.

13. The method of claim 1, wherein the compound exhibits at least 10 times greater activity on a target KCNQ protein in bladder smooth muscle than on a non-target KCNQ protein.

14. The method of claim 1, wherein the compound exhibits at least 100 times greater activity on a target KCNQ protein in bladder smooth muscle than on a non-target KCNQ protein.

15. The method of claim 1, wherein the compound exhibits no detectable activity on a non-target KCNQ protein.

16. The method of claim 1, wherein the compound exhibits at least 2 times greater activity on a target KCNQ protein in bladder smooth muscle than on a protein which forms a potassium channel other than a KCNQ protein.

17. The method of claim 1, wherein the compound exhibits at least 10 times greater activity on a target KCNQ protein in bladder smooth muscle than on a protein which forms a potassium channel other than a KCNQ protein.

18. The method of claim 1, wherein the compound exhibits at least 100 times greater activity on a target KCNQ protein in bladder smooth muscle than on a protein which forms a potassium channel other than a KCNQ protein.

19. The method of claim 1, wherein the compound exhibits no detectable activity on a protein which forms a potassium channel other than a KCNQ protein.

20. A method of screening for a compound for the inhibition of urge urinary incontinence comprising:
    (a) expressing a target KCNQ channel in a host cell; and
    (b) detecting activation of said target KCNQ channel in the host cell;
wherein the detection is performed by measuring the membrane potential of the host cell in the presence or absence of said compound and selecting the compound whose presence causes a change in membrane potential of the host cell.

21. The method of claim 20, wherein the host cell is an animal cell.

22. The method of claim 20, wherein the host cell is mammalian.

23. The method of claim 20, wherein the host cell is human.

24. The method of claim 20, wherein the host cell is human embryonic kidney.

25. The method of claim 20, wherein the host cell is HEK293 or a COS cell.

26. The method of claim 20, wherein detection is performed by measuring membrane potential using an electrophysiological technique or a fluorescence technique.

27. The method of claim 20, wherein the compound exhibits at least 2 times greater activity on a target KCNQ channel in bladder smooth muscle than on another target KCNQ channel in tissue other than bladder smooth muscle.

28. The method of claim 20, wherein the compound exhibits at least 10 times greater activity on a target KCNQ channel in bladder smooth muscle than on another target KCNQ channel in tissue other than bladder smooth muscle.

29. The method of claim 20, wherein the compound exhibits at least 100 times greater activity on a target KCNQ channel in bladder smooth muscle than on another target KCNQ channel in tissue other than bladder smooth muscle.

30. The method of claim 20, wherein the compound exhibits no detectable activity on a KCNQ channel in tissue other than bladder smooth muscle.

31. The method of claim 20, wherein the compound exhibits at least 2 times greater activity on a target KCNQ channel in bladder smooth muscle than on a non-target KCNQ channel.

32. The method of claim 20, wherein the compound exhibits at least 10 times greater activity on a target KCNQ channel in bladder smooth muscle than on a non-target KCNQ channel.

33. The method of claim 20, wherein the compound exhibits at least 100 times greater activity on a target KCNQ channel in bladder smooth muscle than on a non-target KCNQ channel.

34. The method of claim 20, wherein the compound exhibits no detectable activity on a non-target KCNQ channel.

35. The method of claim 20, wherein the compound exhibits at least 2 times greater activity on a target KCNQ channel in bladder smooth muscle than on a potassium channel other than a KCNQ channel.

36. The method of claim 20, wherein the compound exhibits at least 10 times greater activity on a target KCNQ channel in bladder smooth muscle than on a potassium channel other than a KCNQ channel.

37. The method of claim 20, wherein the compound exhibits at least 100 times greater activity on a target KCNQ channel in bladder smooth muscle than on a potassium channel other than a KCNQ channel.

38. The method of claim 20, wherein the compound exhibits no detectable activity on a potassium channel other than a KCNQ channel.

39. A method of screening for a compound for the inhibition of urge urinary incontinence comprising:
   (a) recombinantly expressing a target KCNQ channel in a host cell;
   (b) measuring membrane potential of the host cell in the presence or absence of the compound; and
   (c) selecting the compound whose presence causes hyperpolarization of the host cell.

40. The method of claim 39, wherein the host cell is an animal cell.

41. The method of claim 39, wherein the host cell is mammalian.

42. The method of claim 39, wherein the host cell is human.

43. The method of claim 39, wherein the host cell is human embryonic kidney.

44. The method of claim 39, wherein the host cell is HEK293 or a COS cell.

45. The method of claim 39, wherein detection is performed by measuring membrane potential using an electrophysiological technique or a fluorescence technique.

46. The method of claim 39, wherein the selected compound exhibits at least 2 times greater activity on a target KCNQ channel in bladder smooth muscle than on another target KCNQ channel in tissue other than bladder smooth muscle.

47. The method of claim 39, wherein the selected compound exhibits at least 10 times greater activity on a target KCNQ channel in bladder smooth muscle than on another target KCNQ channel in tissue other than bladder smooth muscle.

48. The method of claim 39, wherein the selected compound exhibits at least 100 times greater activity on a target KCNQ channel in bladder smooth muscle than on another target KCNQ channel in tissue other than bladder smooth muscle.

49. The method of claim 39, wherein the selected compound exhibits no detectable activity on a KCNQ channel in tissue other than bladder smooth muscle.

50. The method of claim 39, wherein the selected compound exhibits at least 2 times greater activity on a target KCNQ channel in bladder smooth muscle than on a non-target KCNQ channel.

51. The method of claim 39, wherein the selected compound exhibits at least 10 times greater activity on a target KCNQ channel in bladder smooth muscle than on a non-target KCNQ channel.

52. The method of claim 39, wherein the selected compound exhibits at least 100 times greater activity on a target KCNQ channel in bladder smooth muscle than on a non-target KCNQ channel.

53. The method of claim 39, wherein the selected compound exhibits no detectable activity on a non-target KCNQ channel.

54. The method of claim 39, wherein the selected compound exhibits at least 2 times greater activity on a target KCNQ channel in bladder smooth muscle than on a potassium channel other than a KCNQ channel.

55. The method of claim 39, wherein the selected compound exhibits at least 10 times greater activity on a target KCNQ channel in bladder smooth muscle than on a potassium channel other than a KCNQ channel.

56. The method of claim 39, wherein the selected compound exhibits at least 100 times greater activity on a target KCNQ channel in bladder smooth muscle than on a potassium channel other than a KCNQ channel.

57. The method of claim 39, wherein the selected compound exhibits no detectable activity on a potassium channel other than a KCNQ channel.

* * * * *

SEQUENCE LISTING

<160> NUMBER OF SEQ ID NOS: 5

<210> SEQ ID NO 1
<211> LENGTH: 2924
<212> TYPE: DNA
<213> ORGANISM: Homo sapiens

<400> SEQUENCE: 1

```
gcagcttcca tggcctgggg ctgtgagagg cccgggaagg cactgtcttt gcgcctgcac      60
atgtgtgtgt ctggagtgta ggatggcact ggtgccgggc ctgggcttcc tcgagcgtcc     120
caccggctgg aagttgtaga cgcggccctg gacgtgggtg cgcgccaaca ccgggcggcg     180
cgtgctgtag atggagacgc gcgggtctag gctcaccggc ggccagggcc gcgtctacaa     240
cttcctcgag cgtcccaccg gctggaaatg cttcgtttac cacttcgccg tcttcctcat     300
cgtcctggtc tgcctcatct tcagcgtgct gtccaccatc gagcagtatg ccgccctggc     360
cacggggact ctcttctgga tggagatcgt gctggtggtg ttcttcggga cggagtacgt     420
ggtccgcctc tggtccgccg gctgccgcag caagtacgtg ggcctctggg ggcggctgcg     480
ctttgcccgg aagcccattt ccatcatcga cctcatcgtg tcgtggcct ccatggtggt     540 cctctgcgtg ggctccaagg ggcaggtgtt tgccacgtcg gccatcaggg gcatccgctt     600
cctgcagatc ctgaggatgc tacacgtcga ccgccaggga ggcacctgga ggctcctggg     660
ctccgtggtc ttcatccacc gccaggagct gataaccacc ctgtacatcg gcttcctggg     720
cctcatcttc tcctcgtact ttgtgtacct ggctgagaag gacgcggtga acgagtcagg     780
ccgcgtggag ttcggcagct acgcagatgc gctgtggtgg ggggtggtca cagtcaccac     840
catcggctat ggggacaagg tgccccagac gtgggtcggg aagaccatcg cctcctgctt     900
ctctgtcttt gccatctcct tctttgcgct cccagcgggg attcttggct cggggtttgc     960
cctgaaggtg cagcagaagc agaggcagaa gcacttcaac cggcagatcc cggcggcagc    1020
ctcactcatt cagaccgcat ggaggtgcta tgctgccgag aaccccgact cctccacctg    1080
gaagatctac atccggaagg ccccccggag ccacactctg ctgtcaccca gccccaaacc    1140
caagaagtct gtggtggtaa agaaaaaaaa gttcaagctg gacaaagaca atgggggtgac    1200 tcctggagag aagatgctca cagtcccccca tatcacgtgc gacccccag aagagcggcg    1260
```

-continued

```
gctggaccac ttctctgtcg acggctatga cagttctgta aggaagagcc caacactgct     1320
ggaagtgagc atgccccatt tcatgagaac caacagcttc gccgaggacc tggacctgga     1380
aggggagact ctgctgacac ccatcaccca catctcacag ctgcgggaac caatcgggc      1440 caccattaag gtcattcgac gcatgcagta ctttgtggcc aagaagaaat ccagcaagc      1500 gcggaagcct tacgatgtgc gggacgtcat tgagcagtac tcgcagggcc acctcaacct     1560
catggtgcgc atcaaggagc tgcagaggag gctggaccag tccattggga agccctcact     1620
gttcatctcc gtctcagaaa agagcaagga tcgcggcagc aacacgatcg gcgcccgcct     1680
gaaccgagta aagacaagg tgacgcagct ggaccagagg ctggcactca tcaccgacat      1740
gcttcaccag ctgctctcct tgcacggtgg cagcaccccc ggcagcggcg ccccccag      1800 agagggcggg gcccacatca cccagccctg cggcagtggc ggctccgtcg accctgagct     1860
cttcctgccc agcaacaccc tgcccaccta cgagcagctg accgtgccca ggaggggccc     1920
cgatgagggg tcctgaggag gggatggggc tgggggatgg gcctgagtga gagggaggc      1980 caagagtggc cccacctggc cctctctgaa ggaggccacc tcctaaaagg cccagagaga     2040
agagccccac tctcagaggc cccaataccc catggaccat gctgtctggc acagcctgca     2100
cttgggggct cagcaaggcc acctcttcct ggccggtgtg ggggcccgt ctcaggtctg      2160 agttgttacc ccaagcgccc tggcccccac atggtgatgt tgacatcact ggcatggtgg     2220
ttgggaccca gtggcagggc acagggcctg gcccatgtat ggccaggaag tagcacaggc     2280
tgagtgcagg cccaccctgc ttggcccagg gggcttcctg aggggagaca gagcaacccc     2340
tggaccccag cctcaaatcc aggaccctgc caggcacagg cagggcagga ccagcccacg     2400
ctgactacag ggccaccggc aataaaagcc caggagccca tttggagggc ctgggcctgg     2460
ctccctcact ctcaggaaat gctgacccat gggcaggaga ctgtggagac tgctcctgag     2520
cccccagctt ccagcaggag ggacagtctc accatttccc cagggcacgt ggttgagtgg     2580
ggggaacgcc cacttccctg ggttagactg ccagctcttc ctagctggag aggagccctg     2640
cctctccgcc cctgagccca ctgtgcgtgg ggctcccgcc tccaaccct cgcccagtcc      2700 cagcagccag ccaaacacac agaaggggac tgccacctcc ccttgccagc tgctgagccg     2760
cagagaagtg acgttcccta cacaggacag gggttccttc tgggcattac atcgcataga     2820
aatcaataat tgtggtgat ttggatctgt gtttaatga gtttcacagt gtgattttga       2880
ttattaattg tgcaagcttt tcctaataaa cgtggagaat caca                     2924
```

<210> SEQ ID NO 2
<211> LENGTH: 2750
<212> TYPE: DNA
<213> ORGANISM: Homo sapiens

<400> SEQUENCE: 2

```
ccccgctgag cctgagcccg acccggggcg cctcccgcca ggcaccatgg tgcagaagtc       60
gcgcaacggc ggcgtatacc ccggcccgag cggggagaag aagctgaagg tgggcttcgt      120
ggggctggac cccggcgcgc ccgactccac ccgggacggg gcgctgctga tcgccggctc      180
cgaggccccc aagcgcggca gcatcctcag caaacctcgc gcgggcggcg cgggcgccgg      240 gaagccccc aagcgcaacg ccttctaccg caagctgcag aatttcctct acaacgtgct       300
ggagcggccg cgcggctggg cgttcatcta ccacgcctac gtgttcctcc tggttttctc      360
ctgcctcgtg ctgtctgtgt tttccaccat caaggagtat gagaagagct cggaggggc      420
```

```
cctctacatc ctggaaatcg tgactatcgt ggtgttttggc gtggagtact tcgtgcggat    480
ctgggccgca ggctgctgct gccggtaccg tggctggagg gggcggctca agtttgcccg    540
gaaaccgttc tgtgtgattg acatcatggt gctcatcgcc tccattgcgg tgctggccgc    600
cggctcccag ggcaacgtct ttgccacatc tgcgctccgg agcctgcgct tcctgcagat    660
tctgcggatg atccgcatgg accggcgggg aggcacctgg aagctgctgg gctctgtggt    720
ctatgcccac agcaaggagc tggtcactgc ctggtacatc ggcttccttt gtctcatcct    780
ggcctcgttc ctggtgtact tggcagagaa aggggagaac gaccactttg acacctacgc    840
ggatgcactc tggtggggcc tgatcacgct gaccaccatt ggctacgggg acaagtaccc    900
ccagacctgg aacggcaggc tccttgcggc aaccttcacc ctcatcggtg tctccttctt    960
cgcgctgcct gcaggcatct tggggtctgg gtttgccctg aaggttcagg agcaacacag    1020
gcagaagcac tttgagaaga ggcggaaccc ggcagcaggc ctgatccagt cggcctggag    1080
attctacgcc accaacctct cgcgcacaga cctgcactcc acgtggcagt actacgagcg    1140
aacggtcacc gtgcccatgt acagttcgca aactcaaacc tacggggcct ccagacttat    1200 cccccgctg aaccagctgg agctgctgag gaacctcaag agtaaatctg gactcgcttt    1260
caggaaggac ccccgccgg agccgtctcc aagcccccga ggcgtggccg ccaaggggaa    1320
ggggtccccg caggcccaga ctgtgaggcg gtcacccagc gccgaccaga gcctcgagga    1380
cagccccagc aaggtgccca agagctggag cttcgggac cgcagccggg cacgccaggc    1440
tttccgcatc aagggtgccg cgtcacggca gaactcagaa gcaagcctcc ccggagagga    1500
cattgtggat gacaagagct gcccctgcga gtttgtgacc gaggacctga ccccgggcct    1560
caaagtcagc atcagagccg tgtgtgtcat gcggttcctg gtgtccaagc ggaagttcaa    1620
ggagagcctg cggccctacg acgtgatgga cgtcatcgag cagtactcag ccggccacct    1680
ggacatgctg tcccgaatta agagcctgca gtccagagtg accagatcg tggggcgggg    1740 cccagcgatc acggacaagg accgcaccaa gggcccggcc gaggcggagc tgcccgagga    1800
ccccagcatg atgggacggc tcgggaaggt ggagaagcag gtcttgtcca tggaagaa    1860 gctggacttc ctggtgaata tctacatgca gcggatgggc atccccccga cagagaccga    1920
ggcctacttt ggggccaaag agccggagcc ggcgccgccg taccacagcc cggaagacag    1980
ccgggagcat gtcgacaggc acggctgcat tgtcaagatc gtgcgctcca gcagctccac    2040
gggccaggag aacttctcgg cgccccggc cgcgcccct gtccagtgtc cgccctccac    2100
ctcctggcag ccacagagcc acccgcgcca gggcacggcg acctcccccg tggggacca    2160 cggctccctg gtgcgcatcc cgccgccgcc tgcccgcgag cggtcgctgt ccgcctacgg    2220 cggggggcaac cgcgccagca tggagttcct gcggcaggag acaccccgg gctgcaggcc    2280 ccccgagggg aacctgcggg acagcgacac gtccatctcc atcccgtccg tggaccacga    2340
ggagctggag cgttccttca gcggcttcag catctcccag tccaaggaga acctggatgc    2400
tctcaacagc tgctacgcgg ccgtggcgcc ttgtgccaaa gtcaggccct acattgcgga    2460
gggagagtca gacactgact ccgacctctg taccccgtgc gggccccgc catgctcggc    2520 caccggcgag ggtcccttttg gtgacgtggg ctgggccggg cccaggaagt gaggcggcgc    2580
tgggccagtg gacccgcccg cggccctcct cagcacggtg cctccgaggt tttgaggcgg    2640
gaaccctctg ggggccttttt cttacagtaa ctgggtgtgg cgggaagggt gggccctga    2700 ggggcccatg tgggctgaag gatgggggct cctggcagtg acctttaca             2750
```

<210> SEQ ID NO 3
<211> LENGTH: 3005
<212> TYPE: DNA
<213> ORGANISM: Homo sapiens
<220> FEATURE:
<221> NAME/KEY: Unsure
<222> LOCATION: (1)..(5)
<223> OTHER INFORMATION: N is unknown, but could be A, T, G, or C.
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: Unsure
<222> LOCATION: (1460)..(1557)
<223> OTHER INFORMATION: N is unknown, but could be A, T, G, or C.
<220> FEATURE:
<221> NAME/KEY: misc_feature
<222> LOCATION: (1460)..(1557)
<223> OTHER INFORMATION: n is a, c, g, or t

<400> SEQUENCE: 3

```
nnnnngaccc cctgaacccc ctgcctggcc tcccctgccc cccaggggcc cgcctttgcc      60
tgcttttggg gggggtggg gaggggcgcg cggatcatgg cattggagtt cccgggcttg      120
cagccgccgc cgccgcctcg ttcacgcacc ccgagcgccc cttcttccca gagcagcagc     180
ggagaaggcg aagcgttctt cggggcgag gcagatgggg ctcaaggcgc gcagggcggc      240
ggggcggct ggcggcggcg gcgacggggg cggcggaggc ggcggggcgg ctaacccagc      300
cggaggggac gcggcggcgg ccggcgacga ggagcggaaa gtgggctgg cgccggcga      360
cgtggagcaa gtcaccttgg cgctcgggc cggagccgac aaagacggga ccctgctgct      420
ggagggcggc ggccgcgacg agggcagcg gaggaccccg cagggcatcg ggctcctggc      480
caagaccccg ctgagccgcc cagtcaagag aaacaacgcc aagtaccggc gcatccaaac     540
tttgatctac gacgccctgg agagaccgcg gggctgggcg ctgctttacc acgcgttggt     600
gttcctgatt gtcctggggt gcttgattct ggctgtcctg accacattca aggagtatga     660
gactgtctcg ggagactggc ttctgttact ggagacattt gctattttca tctttggagc     720
cgagtttgct ttgaggatct gggctgctgg atgttgctgc cgatacaaag ctggcgggg     780
ccgactgaag tttgccagga agcccctgtg catgttggac atctttgtgc tgattgcctc     840
tgtgccagtg gttgctgtgg aaaccaagg caatgttctg gccacctccc tgcgaagcct     900
gcgcttcctg cagatcctgc gcatgctgcg gatggaccgg agaggtggca cctggaagct     960
tctgggctca gccatctgtg cccacagcaa agaactcatc acggcctggt acatcggttt    1020
cctgacactc atcctttctt catttcttgt ctacctggtt gagaaagacg tcccagaggt    1080
ggatgcacaa ggagaggaga tgaaagagga gtttgagacc tatgcagatg ccctgtggtg    1140
gggcctgatc acactggcca ccattggcta tggagacaag acacccaaaa cgtgggaagg    1200
ccgtctgatt gccgccacct ttccttaat tggcgtctcc ttttttgccc ttccagcggg    1260
catcctgggg tccgggctgg ccctcaaggt gcaggagcaa caccgtcaga agcactttga    1320
gaaaaggagg aagccagctg ctgagctcat tcaggctgcc tggaggtatt atgctaccaa    1380
ccccaacagg attgacctgg tggcgacatg gagatttat gaatcagtcg tctcttttcc    1440
tttcttcagg caagtgggn nnnnnnnnn nnnnnnnnn nnnnnnnnn nnnnnnnnn         1500
nnnnnnnnnn nnnnnnnnn nnnnnnnnn nnnnnnnnn nnnnnnnnn nnnnnnatt         1560
ttgtagccaa aagctgggtc tcttggatcg ggttcgcctt tctaatcctc gtggtagcaa    1620
tactaaagga aagctatttta cccctctgaa tgtagatgcc atagaagaaa gtccttctaa    1680
```

-continued

| | |
|---|---|
| agaaccaaag cctgttggct taaacaataa agagcgtttc cgcacggcct tccgcatgaa | 1740 |
| agcctacgct ttctggcaga gttctgaaga tgccgggaca ggtgacccca tggcggaaga | 1800 |
| caggggctat gggaatgact tccccatcga agacatgatc cccacccctga aggccgccat | 1860 |
| ccgagccgtc agaattctac aattccgtct ctataaaaaa aaattcaagg agactttgag | 1920 |
| gccttacgat gtgaaggatg tgattgagca gtattctgcc gggcatctcg acatgctttc | 1980 |
| caggataaag taccttcaga cgagaataga tatgattttc accctggac ctccctccac | 2040 |
| gccaaaacac aagaagtctc agaaagggtc agcattcacc ttcccatccc agcaatctcc | 2100 |
| caggaatgaa ccatatgtag ccagaccatc cacatcagaa atcgaagacc aaagcatgat | 2160 |
| ggggaagttt gtaaaagttg aaagacaggt tcaggacatg gggaagaagc tggacttcct | 2220 |
| cgtggatatg cacatgcaac acatggaacg gttgcaggtg caggtcacgg agtattaccc | 2280 |
| aaccaagggc acctcctcgc cagctgaagc agagaagaag gaggacaaca ggtattccga | 2340 |
| tttgaaaacc atcatctgca actattctga cacaggcccc ccggaaccac cctacagctt | 2400 |
| ccaccaggtg accattgaca aagtcagccc ctatgggttt tttgcacatg accctgtgaa | 2460 |
| cctgccccga gggggaccca gttctggaaa ggttcaggca actcctcctt cctcagcaac | 2520 |
| aacgtatgtg gagaggccca cggtcctgcc tatcttgact cttctcgact cccgagtgag | 2580 |
| ctgccactcc caggctgacc tgcagggccc tactcggac cgaatctccc ccggcagag | 2640 |
| acgtagcatc acgcgagaca gtgacacacc tctgtccctg atgtcggtca accacgagga | 2700 |
| gctggagagg tctccaagtg gcttcagcat ctcccaggac agagatgatt atgtgttcgg | 2760 |
| ccccaatggg gggtcgagct ggatgaggga gaagcggtac ctcgccgagg gtgagacgga | 2820 |
| cacagacacg gacccctttca cgcccagcgg ctccatgcct ctgtcgtcca caggggatgg | 2880 |
| gatttctgat tcagtatgga cccctttccaa taagcccatt taaaagaggt cactggctga | 2940 |
| cccctccttg taatgtagac agactttgta tagttcactt actcttacac ccgacgctta | 3000 |
| ccagc | 3005 |

<210> SEQ ID NO 4
<211> LENGTH: 2335
<212> TYPE: DNA
<213> ORGANISM: Homo sapiens

<400> SEQUENCE: 4

| | |
|---|---|
| agccatgcgt ctctgagcgc cccgagcgcg ccccgcccc ggaccgtgcc cgggccccgg | 60 |
| cgcccccagc ccggcgccgc ccatggccga ggccccccg cgccgcctcg gcctgggtcc | 120 |
| cccgcccggg gacgccccccc gcgcggagct agtggcgctc acggccgtgc agagcgaaca | 180 |
| gggcgaggcg ggcggggggcg gctccccgcg ccgcctcggc ctcctgggca gccccctgcc | 240 |
| gccgggcgcg cccctccctg gccgggctc cggctcgggc tccgcctgcg gccagcgctc | 300 |
| ctcggccgca cacaagcgct accgccgcct gcagaactgg gtctacaacg tgctggagcg | 360 |
| gccccgcggc tgggccttcg tctaccacgt cttcatattt tgctggtct tcagctgcct | 420 |
| ggtgctgtct gtgctgtcca ctatccagga gcaccaggaa cttgccaacg agtgtctcct | 480 |
| catcttggaa ttcgtgatga tcgtggtttt cggcttggag tacatcgtcc gggtctggtc | 540 |
| cgccggatgc tgctgccgct accgaggatg gcagggtcgc ttccgctttg ccagaaagcc | 600 |
| cttctgtgtc atcgacttca tcgtgttcgt ggcctcggtg gccgtcatcg ccgcgggtac | 660 |
| ccagggcaac atcttcgcca cgtccgcgct gcgcagcatg cgcttcctgc agatcctgcg | 720 |
| catggtgcgc atggaccgcc gcggcggcac ctggaagctg ctgggctcag tggtctacgc | 780 |

-continued

```
gcatagcaag gagctgatca ccgcctggta catcgggttc ctggtgctca tcttcgcctc      840
cttcctggtc tacctggccg agaaggacgc caactccgac ttctcctcct acgccgactc      900
gctctggtgg gggacgatta cattgacaac atcggctat ggtgacaaga caccgcacac       960
atggctgggc agggtcctgg ctgctggctt cgccttactg gcatctctt tctttgccct      1020 gcctgccggc atcctaggct ccggctttgc cctgaaggtc caggagcagc accggcagaa     1080
gcacttcgag aagcggagga tgccggcagc caacctcatc caggctgcct ggcgcctgta     1140
ctccaccgat atgagccggg cctacctgac agccacctgg tactactatg acagtatcct     1200
cccatccttc agagagctgg ccctcttgtt tgagcacgtg caacgggccc gcaatggggg     1260
cctacggccc ctggaggtgc ggcgggcgcc ggtacccgac ggagcaccct cccgttaccc     1320
gcccgttgcc acctgccacc ggccgggcag cacctccttc tgccctgggg aaagcagccg     1380
gatgggcatc aaagaccgca tccgcatggg cagctcccag cggcggacgg gtccttccaa     1440
gcagcagctg gcacctccaa caatgcccac ctccccaagc agcgagcagg tgggtgaggc     1500
caccagcccc accaaggtgc aaaagagctg gagcttcaat gaccgcaccc gcttccgggc     1560
atctctgaga ctcaaacccc gcacctctgc tgaggatgcc ccctcagagg aagtagcaga     1620
ggagaagagc taccagtgtg agctcacggt ggacgcacatc atgcctgctg tgaagacagt    1680
catccgctcc atcaggattc tcaagttcct ggtggccaaa aggaaattca aggagacact     1740
gcgaccgtac gacgtgaagg acgtcattga gcagtactca gcaggccacc tggacatgct     1800
gggccggatc aagagcctgc aaactcgggt ggaccaaatt gtgggtcggg ggcccgggga     1860
caggaaggcc cggagaagg gcgacaaggg gccctccgac gcggaggtgg tggatgaaat      1920
cagcatgatg ggacgcgtgg tcaaggtgga aagcaggtg cagtccatcg agcacaagct     1980
ggacctgctg ttgggcttct attcgcgctg cctgcgctct ggcacctcgg ccagcctggg    2040
cgccgtgcaa gtgccgctgt cgaccccga catcacctcc gactaccaca gccctgtgga     2100
ccacgaggac atctccgtct ccgcacagac gctcagcatc tcccgctcgg tcagcaccaa    2160
catggactga gggacttctc agaggcaggg cagcacacgg ccagccccgc ggcctggcgc    2220
tccgactgcc ctctgaggcc tccggactcc tctcgtactt gaactcactc cctcacgggg    2280
agagagacca cacgcagtat tgagctgcct gagtgggcgt ggtacctgct gtggg         2335
```

<210> SEQ ID NO 5
<211> LENGTH: 3074
<212> TYPE: DNA
<213> ORGANISM: Homo sapiens

<400> SEQUENCE: 5

```
gggcgccccg tcggccgccg gcttcctcct tgaaacccgc cggcgcacat gaggccgctg       60 ccccgccgc aggcgctggc ggcccccctcg cggtgcccgt ggtgatgcca tgccccgcca     120
ccacgcggga ggagaggagg gcggcgccgc cgggctctgg gtgaagagcg gcgcagcggc     180
ggcggcggcg gcgggggggc gcttgggcag cggcatgaag gatgtggagt cgggccgggg     240
cagggtgctg ctgaactcgg cagccgccag gggcgacggc ctgctactgc tgggcacccg     300
cgcggccacg cttggtggcg gcggcggtgg cctgagggag agccgccggg gcaagcaggg     360
ggcccggatg agcctgctgg gaagccgcct ctcttacacg agtagccaga gctgccggcg     420
caacgtcaag taccgcgggg tgcagaacta cctgtacaac gtgctggaga ccccgcggg     480 ctgggcgttc atctaccacg ctttcgtttt cctccttgtc tttggttgct tgattttgtc     540
```

-continued

```
agtgttttct accatccctg agcacacaaa attggcctca agttgcctct tgatcctgga      600
gttcgtgatg attgtcgtct ttggtttgga gttcatcatt cgaatctggt ctgcgggttg      660
ctgttgtcga tatagaggat ggcaaggaag actgaggttt gctcgaaagc ccttctgtgt      720
tatagatacc attgttctta tcgcttcaat agcagttgtt tctgcaaaaa ctcagggtaa      780
tattttttgcc acgtctgcac tcagaagtct ccgtttccta cagatcctcc gcatggtgcg      840
catggaccga aggggaggca cttggaaatt actgggttca gtggtttatg ctcacagcaa      900
ggaattaatc acagcttggt acataggatt tttggttctt atttttttcgt ctttccttgt      960
ctatctggtg gaaaaggatg ccaataaaga gttttctaca tatgcagatg ctctctggtg     1020
gggcacaatt acattgacaa ctattggcta tggagacaaa actcccctaa cttggctggg     1080
aagattgctt tctgcaggct ttgcactcct tggcatttct ttcttttgcac ttcctgccgg     1140
cattcttggc tcaggttttg cattaaaagt acaagaacaa caccgccaga aacactttga     1200
gaaaagaagg aacccagctg ccaacctcat tcagtgtgtt tggcgtagtt acgcagctga     1260
tgagaaatct gtttccattg caacctggaa gccacacttg aaggccttgc acacctgcag     1320
ccctaccaag aaagaacaag gggaagcatc aagcagtcag aagctaagtt ttaaggagcg     1380
agtgcgcatg gctagcccca ggggccagag tattaagagc cgacaagcct cagtaggtga     1440
caggaggtcc ccaagcaccg acatcacagc cgagggcagt cccaccaaag tgcagaagag     1500
ctggagcttc aacgaccgaa cccgcttccg gccctcgctg cgcctcaaaa gttctcagcc     1560
aaaaccagtg atagatgctg acacagccct tggcactgat gatgtatatg atgaaaaagg     1620
atgccagtgt gatgtatcag tggaagacct cacccccacca cttaaaactg tcattcgagc     1680
tatcagaatt atgaaatttc atgttgcaaa acggaagttt aaggaaacat acgtccata      1740
tgatgtaaaaa gatgtcattg aacaatattc tgctggtcat ctggacatgt tgtgtagaat     1800
taaaagccttt caaacacgtg ttgatcaaat tcttggaaaaa gggcaaatca catcagataa     1860
gaagagccga gagaaaataa cagcagaaca tgagaccaca gacgatctca gtatgctcgg     1920
tcgggtggtc aaggttgaaa acaggtaca gtccatagaa tccaagctgg actgcctact      1980
agacatctat caacaggtcc ttcggaaagg ctctgcctca gccctcgctt tggcttcatt     2040
ccagatccca ccttttgaat gtgaacagac atctgactat caaagccctg tggatagcaa     2100
agatctttcg ggttccgcac aaaacagtgg ctgcttatcc agatcaacta gtgccaacat     2160
ctcgagaggc ctgcagttca ttctgacgcc aaatgagttc agtgcccaga ctttctacgc     2220
gcttagccct actatgcaca gtcaagcaac acaggtgcca attagtcaaa gcgatggctc     2280
agcagtggca gccaccaaca ccattgcaaa ccaaataaat acggcaccca agccagcagc     2340
cccaacaact ttacagatcc cacctcctct cccagccatc aagcatctgc ccaggccaga     2400
aactctgcac cctaaccctg caggcttaca ggaaagcatt tctgacgtca ccacctgcct     2460
tgttgcctcc aaggaaaatg ttcaggttgc acagtcaaat ctcaccaagg accgttctat     2520
gaggaaaagc tttgacatgg gaggagaaac tctgttgtct gtctgtccca tggtgccgaa     2580
ggacttgggc aaatctttgt ctgtgcaaaa cctgatcagg tcgaccgagg aactgaatat     2640
acaactttca gggagtgagt caagtggctc cagaggcagc caagattttt accccaaatg     2700
gagggaatcc aaattgttta taactgatga agaggtgggt cccgaagaga cagagacaga     2760
cacttttgat gccgcaccgc agcctgccag ggaagctgcc tttgcatcag actctctaag     2820
gactggaagg tcacgatcat ctcagagcat ttgtaaggca ggagaaagta cagatgccct     2880
cagcttgcct catgtcaaac tgaaataagt tcttcatttt ctttccaggc atagcagttc     2940
```

```
                                           -continued tttagccata catatcattg catgaactat ttcgaaagcc cttctaaaaa gttgaaattg    3000
caagaatcgg gaagaacatg aaaggcagtt tataagcccg ttacctttta attgcatgaa    3060
aatgcatgtt tagg                                                     3074
```